(12) United States Patent
Swart et al.

(10) Patent No.: US 8,990,098 B2
(45) Date of Patent: *Mar. 24, 2015

(54) VALIDATED HEALTHCARE CLEANING AND SANITIZING PRACTICES

(75) Inventors: Sally K. Swart, Rosemount, MN (US); Ryan D. Meek, Cottage Grove, MN (US); Kirsten M. Thompson, Northfield, MN (US); Kimberly Severin Johnston, St. Paul Park, MN (US); Henry L. Carbone, II, St. Paul, MN (US); Scott P. Lyon, Eagan, MN (US); John R. Bucholz, Woodbury, MN (US)

(73) Assignee: Ecolab Inc., St. Paul, MN (US)

( * ) Notice: Subject to any disclaimer, the term of this patent is extended or adjusted under 35 U.S.C. 154(b) by 420 days.

This patent is subject to a terminal disclaimer.

(21) Appl. No.: 12/432,277

(22) Filed: Apr. 29, 2009

(65) Prior Publication Data

US 2009/0276239 A1 Nov. 5, 2009

Related U.S. Application Data

(60) Provisional application No. 61/125,922, filed on Apr. 30, 2008.

(51) Int. Cl.
 *G06Q 10/00* (2012.01)
 *G06Q 50/00* (2012.01)
 (Continued)

(52) U.S. Cl.
 CPC .............. *A61L 2/00* (2013.01); *G06F 19/327* (2013.01); *G06Q 10/06375* (2013.01); *G06Q 50/22* (2013.01)
 USPC .......................................................... 705/2

(58) Field of Classification Search
 CPC .............................. G06Q 50/22; G06F 19/327
 USPC .......................................................... 705/2, 3
 See application file for complete search history.

(56) References Cited

U.S. PATENT DOCUMENTS

| 3,736,584 A | 5/1973 | Hackett et al. |
| 3,761,909 A | 9/1973 | Schweitzer et al. |

(Continued)

FOREIGN PATENT DOCUMENTS

| DE | 19882120 B4 | 10/2010 |
| EP | 0921506 A1 | 6/1999 |

(Continued)

OTHER PUBLICATIONS

Chris Griffith, "Nosocomial infection, Are there lessons from the food industry?", The Biomedical Scientist, pp. 697-699, Aug. 2006.

(Continued)

*Primary Examiner* — John Pauls
*Assistant Examiner* — Trang Nguyen
(74) *Attorney, Agent, or Firm* — Shumaker & Sieffert, P.A.

(57) ABSTRACT

A validated healthcare facility cleaning and sanitizing system provides a comprehensive and systematic approach to cleaning and sanitizing practices at a hospital or other healthcare facility. The validated hospital cleaning system identifies hospital vectors of contamination; that is, sources through which hospital acquired infections (HAIs) may be spread. The validated system defines a plurality of modules within a healthcare facility, each having an associated cleaning process map designed to meet the particular cleaning and/or sanitizing needs and challenges faced by that module. Various stages of the cleaning process map include validation points, at which certain parameters designed to ensure proper cleaning and/or sanitizing of the module are verified.

28 Claims, 30 Drawing Sheets

(51) Int. Cl.
*A61L 2/00* (2006.01)
*G06F 19/00* (2011.01)
*G06Q 10/06* (2012.01)
*G06Q 50/22* (2012.01)

(56) References Cited

U.S. PATENT DOCUMENTS

| | | |
|---|---|---|
| 3,786,467 A | 1/1974 | Cotter |
| 3,801,977 A | 4/1974 | Cotter |
| 3,866,198 A | 2/1975 | Cohen |
| 3,961,321 A | 6/1976 | Moss |
| 3,986,182 A | 10/1976 | Hackett |
| 4,076,146 A | 2/1978 | Lausberg et al. |
| 4,117,462 A | 9/1978 | Miller |
| 4,198,618 A | 4/1980 | Kleinschmidt |
| 4,209,776 A | 6/1980 | Frederick |
| 4,275,390 A | 6/1981 | Heywang et al. |
| 4,319,349 A | 3/1982 | Hackett |
| 4,360,905 A | 11/1982 | Hackett |
| 4,486,910 A | 12/1984 | Saalmann et al. |
| 4,539,846 A | 9/1985 | Grossman |
| 4,590,460 A | 5/1986 | Abbott et al. |
| 4,644,509 A | 2/1987 | Kiewit et al. |
| 4,727,522 A | 2/1988 | Steiner et al. |
| 4,729,120 A | 3/1988 | Steiner et al. |
| 4,896,144 A | 1/1990 | Bogstad |
| 4,987,402 A | 1/1991 | Nykerk |
| 4,991,146 A | 2/1991 | Ransdell et al. |
| 5,083,298 A | 1/1992 | Citterio et al. |
| 5,110,364 A | 5/1992 | Mazur et al. |
| 5,150,099 A | 9/1992 | Lienau |
| 5,153,520 A | 10/1992 | Dumbeck |
| 5,202,666 A | 4/1993 | Knippscheer |
| 5,245,317 A | 9/1993 | Chidley et al. |
| 5,263,006 A | 11/1993 | Hermesmeyer |
| 5,309,409 A | 5/1994 | Jones et al. |
| 5,370,267 A | 12/1994 | Schroeder |
| 5,390,385 A | 2/1995 | Beldham |
| 5,430,293 A | 7/1995 | Sato et al. |
| 5,463,595 A | 10/1995 | Rodhall et al. |
| 5,570,079 A | 10/1996 | Dockery |
| 5,610,589 A | 3/1997 | Evans et al. |
| 5,625,659 A | 4/1997 | Sears |
| 5,661,471 A | 8/1997 | Kotlicki |
| 5,684,458 A | 11/1997 | Calvarese |
| 5,695,091 A | 12/1997 | Winings et al. |
| 5,731,526 A | 3/1998 | Kindrick |
| 5,764,136 A | 6/1998 | Harron |
| 5,765,605 A | 6/1998 | Waymire et al. |
| 5,771,925 A | 6/1998 | Lewandowski |
| H1743 H | 8/1998 | Graves et al. |
| 5,793,653 A | 8/1998 | Segal |
| 5,812,059 A | 9/1998 | Shaw et al. |
| 5,900,067 A | 5/1999 | Jones |
| 5,913,915 A | 6/1999 | McQuinn |
| 5,917,425 A | 6/1999 | Crimmins et al. |
| 5,939,974 A | 8/1999 | Heagle et al. |
| 5,945,910 A | 8/1999 | Gorra |
| 5,952,924 A | 9/1999 | Evans et al. |
| 5,954,069 A | 9/1999 | Foster |
| 5,966,753 A | 10/1999 | Gauthier et al. |
| 5,977,913 A | 11/1999 | Christ |
| 5,979,703 A | 11/1999 | Nystrom |
| 5,987,105 A | 11/1999 | Jenkins et al. |
| 6,012,041 A | 1/2000 | Brewer et al. |
| 6,031,461 A | 2/2000 | Lynn |
| 6,038,331 A | 3/2000 | Johnson |
| 6,065,639 A | 5/2000 | Maddox et al. |
| 6,125,482 A | 10/2000 | Foster |
| 6,130,607 A | 10/2000 | McClanahan et al. |
| 6,147,607 A | 11/2000 | Lynn |
| 6,175,308 B1 | 1/2001 | Tallman et al. |
| 6,191,693 B1 | 2/2001 | Sangsingkeow |
| 6,211,788 B1 | 4/2001 | Lynn et al. |
| 6,213,424 B1 | 4/2001 | Helfer-Grand |
| 6,236,317 B1 | 5/2001 | Cohen et al. |
| 6,236,953 B1 | 5/2001 | Segal |
| 6,259,956 B1 | 7/2001 | Myers et al. |
| 6,278,372 B1 | 8/2001 | Velasco, Jr. et al. |
| 6,279,777 B1 | 8/2001 | Goodin et al. |
| 6,288,641 B1 | 9/2001 | Casais |
| 6,314,282 B1 | 11/2001 | Weber et al. |
| 6,331,964 B1 | 12/2001 | Barone |
| 6,351,223 B1 | 2/2002 | DeWeerd et al. |
| 6,360,181 B1 | 3/2002 | Gemmell et al. |
| 6,368,420 B1 | 4/2002 | Angevaare et al. |
| 6,375,038 B1 | 4/2002 | Daansen et al. |
| 6,392,546 B1 | 5/2002 | Smith |
| 6,404,837 B1 | 6/2002 | Thompson et al. |
| 6,417,773 B1 | 7/2002 | Vlahos et al. |
| 6,426,701 B1 | 7/2002 | Levy et al. |
| 6,476,385 B1 | 11/2002 | Albert |
| 6,485,979 B1 | 11/2002 | Kippenhan et al. |
| 6,523,193 B2 | 2/2003 | Saraya |
| 6,524,390 B1 | 2/2003 | Jones |
| 6,577,240 B2 | 6/2003 | Armstrong |
| 6,611,207 B1 | 8/2003 | Yuan et al. |
| 6,681,003 B2 | 1/2004 | Linder et al. |
| 6,707,873 B2 | 3/2004 | Thompson et al. |
| 6,727,818 B1 | 4/2004 | Wildman et al. |
| 6,730,024 B2 | 5/2004 | Freyre et al. |
| 6,749,148 B2 | 6/2004 | Helfer-Grand |
| 6,759,959 B2 | 7/2004 | Wildman |
| 6,778,092 B2 | 8/2004 | Braune |
| 6,781,523 B2 | 8/2004 | Matsui et al. |
| 6,792,395 B2 | 9/2004 | Roberts |
| 6,799,085 B1 | 9/2004 | Crisp, III |
| 6,882,278 B2 | 4/2005 | Winings et al. |
| 6,882,315 B2 | 4/2005 | Richley et al. |
| 6,883,563 B2 | 4/2005 | Smith |
| 6,917,290 B2 | 7/2005 | Land |
| 6,919,567 B2 | 7/2005 | Iwasawa |
| 6,956,498 B1 | 10/2005 | Gauthier et al. |
| 6,975,231 B2 | 12/2005 | Lane et al. |
| 7,015,816 B2 | 3/2006 | Wildman et al. |
| 7,023,356 B2 | 4/2006 | Burkhardt et al. |
| 7,042,361 B2 | 5/2006 | Kazdin et al. |
| 7,056,050 B2 | 6/2006 | Sacks |
| 7,067,054 B2 | 6/2006 | Fritze |
| 7,069,188 B2 | 6/2006 | Roberts |
| 7,075,412 B1 | 7/2006 | Reynolds et al. |
| 7,099,781 B1 | 8/2006 | Heidl et al. |
| 7,099,856 B2 | 8/2006 | Barangan et al. |
| 7,117,374 B2 | 10/2006 | Hill et al. |
| 7,119,688 B2 | 10/2006 | Wildman |
| 7,119,692 B2 | 10/2006 | Leiffort et al. |
| 7,142,108 B2 | 11/2006 | Diener et al. |
| 7,157,045 B2 | 1/2007 | McVey |
| 7,187,287 B2 | 3/2007 | Ryal |
| 7,191,090 B1 | 3/2007 | Cunningham |
| 7,201,005 B2 | 4/2007 | Voglewede et al. |
| 7,202,780 B2 | 4/2007 | Teller |
| 7,236,097 B1 | 6/2007 | Cunningham |
| 7,242,307 B1 | 7/2007 | LeBlond et al. |
| 7,248,933 B2 | 7/2007 | Wildman |
| 7,265,673 B2 | 9/2007 | Teller |
| 7,266,347 B2 | 9/2007 | Gross |
| 7,267,531 B2 | 9/2007 | Anderson et al. |
| 7,271,728 B2 | 9/2007 | Taylor et al. |
| 7,272,537 B2 | 9/2007 | Mogadam |
| 7,286,057 B2 | 10/2007 | Bolling |
| 7,292,914 B2 | 11/2007 | Jungmann et al. |
| 7,293,645 B2 | 11/2007 | Harper et al. |
| 7,315,245 B2 | 1/2008 | Lynn et al. |
| 7,330,108 B2 | 2/2008 | Thomas |
| 7,372,367 B2 | 5/2008 | Lane et al. |
| 7,375,640 B1 | 5/2008 | Plost |
| 7,400,264 B2 | 7/2008 | Boaz |
| 7,408,470 B2 | 8/2008 | Wildman et al. |
| 7,411,511 B2 | 8/2008 | Kennish et al. |
| 7,423,533 B1 * | 9/2008 | LeBlond et al. ............ 340/572.1 |
| 7,425,900 B2 | 9/2008 | Lynn et al. |
| 7,440,620 B1 | 10/2008 | Aartsen |
| 7,443,305 B2 | 10/2008 | Verdiramo |

(56) References Cited

U.S. PATENT DOCUMENTS

| | | | |
|---|---|---|---|
| 7,450,472 B2 | 11/2008 | Guyvarch |
| 7,457,869 B2 | 11/2008 | Kernan |
| 7,474,215 B2 | 1/2009 | Scott et al. |
| 7,477,148 B2 | 1/2009 | Lynn et al. |
| 7,482,936 B2 | 1/2009 | Bolling |
| 7,486,193 B2 | 2/2009 | Elwell |
| 7,487,538 B2 | 2/2009 | Mok |
| 7,490,045 B1 | 2/2009 | Flores et al. |
| 7,496,479 B2 | 2/2009 | Garcia et al. |
| 7,538,680 B2 | 5/2009 | Scott et al. |
| 7,551,092 B1 | 6/2009 | Henry |
| 7,597,122 B1 | 10/2009 | Smith |
| 7,600,137 B2 | 10/2009 | Trappeniers et al. |
| 7,605,704 B2 | 10/2009 | Munro et al. |
| 7,611,030 B2 | 11/2009 | Reynolds et al. |
| 7,616,122 B2 | 11/2009 | Bolling |
| 7,718,395 B2 | 5/2010 | Carling |
| 7,780,453 B2 | 8/2010 | Carling |
| 7,785,109 B2 | 8/2010 | Carling |
| 2001/0039501 A1 | 11/2001 | Crevel et al. |
| 2001/0047214 A1 | 11/2001 | Cocking et al. |
| 2001/0053939 A1 | 12/2001 | Crevel et al. |
| 2001/0054038 A1 | 12/2001 | Crevel et al. |
| 2002/0000449 A1 | 1/2002 | Armstrong |
| 2002/0019709 A1 | 2/2002 | Segal |
| 2002/0050006 A1 | 5/2002 | Saraya |
| 2002/0103671 A1 | 8/2002 | Pederson et al. |
| 2002/0132343 A1* | 9/2002 | Lum ............................ 435/372 |
| 2002/0135486 A1 | 9/2002 | Brohagen et al. |
| 2002/0145523 A1 | 10/2002 | Robaey |
| 2002/0175182 A1 | 11/2002 | Matthews et al. |
| 2002/0183979 A1 | 12/2002 | Wildman |
| 2003/0030562 A1 | 2/2003 | Lane et al. |
| 2003/0065536 A1 | 4/2003 | Hansen et al. |
| 2003/0074222 A1* | 4/2003 | Rosow et al. ...................... 705/2 |
| 2003/0182180 A1 | 9/2003 | Zarrow |
| 2004/0001009 A1 | 1/2004 | Winings et al. |
| 2004/0015269 A1 | 1/2004 | Jungmann et al. |
| 2004/0028608 A1 | 2/2004 | Saul et al. |
| 2004/0049369 A1 | 3/2004 | Konicek et al. |
| 2004/0075347 A1 | 4/2004 | Biskup, Sr. et al. |
| 2004/0088076 A1 | 5/2004 | Gardner, Jr. |
| 2004/0090333 A1 | 5/2004 | Wildman et al. |
| 2004/0148196 A1 | 7/2004 | Kalies |
| 2004/0162850 A1 | 8/2004 | Sanville et al. |
| 2005/0086341 A1 | 4/2005 | Enga et al. |
| 2005/0102167 A1 | 5/2005 | Kapoor |
| 2005/0149341 A1 | 7/2005 | Eguchi et al. |
| 2005/0222889 A1 | 10/2005 | Lai et al. |
| 2006/0067545 A1 | 3/2006 | Lewis et al. |
| 2006/0067546 A1 | 3/2006 | Lewis et al. |
| 2006/0071799 A1 | 4/2006 | Verdiramo |
| 2006/0104245 A1 | 5/2006 | Narayanaswami et al. |
| 2006/0132316 A1 | 6/2006 | Wildman et al. |
| 2006/0139449 A1 | 6/2006 | Cheng et al. |
| 2006/0140703 A1* | 6/2006 | Sacks ............................ 401/139 |
| 2006/0154642 A1 | 7/2006 | Scannell, Jr. |
| 2006/0223731 A1* | 10/2006 | Carling ......................... 510/156 |
| 2006/0229821 A1 | 10/2006 | Brossette et al. |
| 2006/0272361 A1 | 12/2006 | Snodgrass |
| 2006/0273915 A1 | 12/2006 | Snodgrass |
| 2007/0008146 A1 | 1/2007 | Taylor et al. |
| 2007/0008147 A1 | 1/2007 | Bolling |
| 2007/0008149 A1 | 1/2007 | Bolling |
| 2007/0016466 A1 | 1/2007 | Taylor |
| 2007/0020212 A1 | 1/2007 | Bernal et al. |
| 2007/0029962 A1 | 2/2007 | Saeki |
| 2007/0044819 A1 | 3/2007 | Chan et al. |
| 2007/0055483 A1 | 3/2007 | Lee et al. |
| 2007/0056091 A1 | 3/2007 | Bolton et al. |
| 2007/0069884 A1 | 3/2007 | Waxman |
| 2007/0096930 A1 | 5/2007 | Cardoso |
| 2007/0182581 A1 | 8/2007 | Elwell |
| 2007/0198067 A1 | 8/2007 | Van den Heuvel et al. |
| 2007/0205861 A1 | 9/2007 | Nair et al. |
| 2007/0213877 A1 | 9/2007 | Hart et al. |
| 2007/0222599 A1 | 9/2007 | Coveley et al. |
| 2007/0229288 A1 | 10/2007 | Ogrin et al. |
| 2007/0247316 A1 | 10/2007 | Wildman et al. |
| 2007/0257803 A1 | 11/2007 | Munro et al. |
| 2007/0285277 A1 | 12/2007 | Scott et al. |
| 2007/0290865 A1 | 12/2007 | Lynn et al. |
| 2008/0001763 A1 | 1/2008 | Raja et al. |
| 2008/0019489 A1 | 1/2008 | Lynn |
| 2008/0046278 A1 | 2/2008 | Sanville et al. |
| 2008/0084315 A1 | 4/2008 | Pittz |
| 2008/0087719 A1 | 4/2008 | Sahud |
| 2008/0100441 A1 | 5/2008 | Prodanovich et al. |
| 2008/0103636 A1* | 5/2008 | Glenn et al. ................... 700/302 |
| 2008/0131332 A1 | 6/2008 | Nguyen et al. |
| 2008/0185540 A1 | 8/2008 | Turner et al. |
| 2008/0189142 A1 | 8/2008 | Brown et al. |
| 2008/0193631 A1* | 8/2008 | Kanamori et al. ............. 427/2.1 |
| 2008/0246599 A1 | 10/2008 | Hufton et al. |
| 2008/0266113 A1 | 10/2008 | Kennish et al. |
| 2008/0280380 A1 | 11/2008 | Dietz et al. |
| 2008/0303658 A1 | 12/2008 | Melker et al. |
| 2009/0002644 A1 | 1/2009 | Christensen et al. |
| 2009/0019552 A1 | 1/2009 | McLaughlin et al. |
| 2009/0051545 A1 | 2/2009 | Koblasz |
| 2009/0091458 A1 | 4/2009 | Deutsch |
| 2009/0102681 A1 | 4/2009 | Brennan, Jr. et al. |
| 2009/0112630 A1 | 4/2009 | Collins, Jr. et al. |
| 2009/0119142 A1* | 5/2009 | Yenni et al. ........................ 705/7 |
| 2009/0138303 A1 | 5/2009 | Seshadri |
| 2009/0195385 A1 | 8/2009 | Huang et al. |
| 2009/0204256 A1 | 8/2009 | Wegelin |
| 2009/0219131 A1 | 9/2009 | Barnett et al. |
| 2009/0219172 A1 | 9/2009 | Wilbrod |
| 2009/0224907 A1 | 9/2009 | Sinha et al. |
| 2009/0224924 A1 | 9/2009 | Thorp |
| 2009/0267776 A1 | 10/2009 | Glenn et al. |
| 2010/0233020 A1 | 9/2010 | Klaassen et al. |
| 2010/0274640 A1 | 10/2010 | Morey et al. |
| 2010/0315243 A1 | 12/2010 | Tokhtuev et al. |
| 2010/0315244 A1 | 12/2010 | Tokhtuev et al. |

FOREIGN PATENT DOCUMENTS

| | | |
|---|---|---|
| EP | 1099400 A2 | 5/2001 |
| EP | 1201172 A2 | 5/2002 |
| EP | 1390204 B1 | 12/2004 |
| EP | 1034132 B1 | 8/2005 |
| EP | 1483728 B1 | 10/2006 |
| EP | 1791077 A2 | 5/2007 |
| EP | 1872802 A1 | 1/2008 |
| EP | 1913892 A2 | 4/2008 |
| GB | 2137749 A | 10/1984 |
| GB | 2217013 A | 10/1989 |
| GB | 2299405 A | 10/1996 |
| GB | 2324397 A | 10/1998 |
| GB | 2337327 A | 11/1999 |
| GB | 2340647 A | 2/2000 |
| GB | 2394654 A | 5/2004 |
| GB | 2417810 A | 3/2006 |
| GB | 2417811 A | 3/2006 |
| GB | 2425388 A | 10/2006 |
| GB | 2446871 A | 8/2007 |
| GB | 2437555 A | 10/2007 |
| GB | 2439306 A | 12/2007 |
| GB | 2439457 A | 12/2007 |
| JP | 10309540 A | 11/1998 |
| JP | 2003105819 A | 4/2003 |
| JP | 2003122823 A | 4/2003 |
| JP | 2005218999 A | 8/2005 |
| JP | 2006198318 A | 8/2006 |
| WO | WO 92/13327 A1 | 8/1992 |
| WO | WO 97/31350 A1 | 8/1997 |
| WO | WO 98/09261 A1 | 3/1998 |
| WO | WO 98/36258 A2 | 8/1998 |
| WO | WO 00/22260 A1 | 4/2000 |
| WO | WO 01/33529 A1 | 5/2001 |
| WO | WO0221475 A1 | 3/2002 |
| WO | WO 03/079278 A1 | 9/2003 |

(56) References Cited

FOREIGN PATENT DOCUMENTS

| WO | WO 03/082351 A2 | 10/2003 |
|---|---|---|
| WO | WO 2005/055793 A2 | 6/2005 |
| WO | WO 2005/055793 A3 | 6/2005 |
| WO | WO 2005/094711 A2 | 10/2005 |
| WO | WO 2006/036687 A1 | 4/2006 |
| WO | WO 2007/001866 A2 | 1/2007 |
| WO | WO 2007/090470 A1 | 8/2007 |
| WO | WO2006135922 A3 | 8/2007 |
| WO | WO 2007/129289 A1 | 11/2007 |
| WO | WO 2007/133960 A2 | 11/2007 |
| WO | WO 2008/088424 A1 | 7/2008 |
| WO | WO 2008/133495 A1 | 11/2008 |
| WO | WO 2010/101929 A2 | 9/2010 |

OTHER PUBLICATIONS

John Bourn, Auditor General for Wales, "The Management and Delivery of Hospital Cleaning Services in Wales", National Audit Office Wales, 39 pages, May 23, 2003.

Mallow General Hospital, "Hygiene Services Assessment Scheme, Assessment Report", 38 pages, Oct. 2007.

Dix et al., "Environmental Surface Cleaning, First Defense Against Infectious Agents", Infection Control Today Magazine, 6 pages, Dec. 1, 2005.

Yoshikura, "Workflow from Clean to Dirty. HACCP and Inclusiveness Principles in Effective Implementation of Hospital Infection Control", Jpn. J. Infect. Dis., vol. 53, pp. 124-125, 2000.

R. Quattrin, MD et al., "Application of Hazard Analysis Critical Control Points to Control Surgical Site Infections in Hip and Knee Arthroplasty", Orthopedics, 31:132, SLACK Incorporated, 6 pgs, 2008.

International Search Report and Written Opinion of the International Searching Authority from corresponding PCT Application Serial No. PCT/IB2009/051751 mailed Jan. 27, 2010 (8 pages).

SaferCorp, LLC, *SaferCorp Life Advantage Solutions presents SaferHands™ Hospital Automated Hand Hygiene Monitoring System*, retrieved electronically from http://www.guardianics.com/ on Dec. 15, 2010, 14 pp.

SaferCorp, LLC, Guardian™ Automated Infection Control Systems (GAICS), Feb. 6, 2010, 4 pp.

Sturman et al., "Cornell Hospitality Report: A New Method for Measuring Housekeeping Performance Consistency," CHR Reports, vol. 6, No. 11, Sep. 2006, 15 pp.

Ophardt hygiene, Hygiene Compliance Solutions, 2009, 1 p.

Elliot, "Determining Three Metrics for Cleaning Satisfaction," found at http://www.facilitiesnet.com/equipmentrentaltools/article/Determining-Three-Metrics-for-Cleaning-Satisfaction--7698#, Nov. 2007, 2 pp.

Van Ryzin et al., "Measuring Street Cleanliness: A Comparison of New York City's Scorecard and Results from a Citizen Survey," Public Administration Review 68(2):295-303, Mar./Apr. 2008.

Evaluating Municipal Services: Scorecard Cleanliness Program Prospectus, New York, found at http://www.worldsweeper.com/Street/Profiles/NYCScorecard.pdf, archived Jan. 5, 2009, 20 pp.

Office Action from U.S. Appl. No. 12/766,714, dated Mar. 29, 2012, 20 pp.

Response to Office Action dated Mar. 29, 2012, from U.S. Appl. No. 12/766,714, filed Jun. 28, 2012, 8 pp.

Office Action from U.S. Appl. No. 12/787,097, dated Jun. 4, 2012, 5 pp.

Response to Office Action dated Jun. 4, 2012, from U.S. Appl. No. 12/787,097, filed Sep. 4, 2012, 8 pp.

Response to Office Action dated Feb. 5, 2013, from U.S. Appl. No. 13/369,056, filed May 3, 2013, 10 pp.

Response to Final Office Action dated Sep. 17, 2012, from U.S. Appl. No. 12/766,714, filed Dec. 17, 2012, 10 pp.

Office Action from U.S. Appl. No. 12/787,064, dated Dec. 6, 2012, 5 pp.

Notice of Allowance from U.S. Appl. No. 12/787,097, dated Nov. 7, 2012, 8 pp.

Al-Hamad et al., "How Clean is Clean? Proposed Methods for Hospital Cleaning Assessment," Journal of Hospital Infection, vol. 70, Oct. 9, 2008, pp. 328-334.

Lewis et al., "A Modified ATP Benchmark for Evaluating the Cleaning of Some Hospital Environmental Surfaces," Journal of Hospital Infection, vol. 69, May 12, 2008, pp. 156-163.

Exner et al., "Household Cleaning and Surface Disinfection: New Insights and Strategies," Journal of Hospital Infection, vol. 56, 2008, pp. s70-s75.

Griffith et al., "The Effectiveness of Existing and Modified Cleaning Regimens in a Welsh Hospital," Journal of Hospital Infection, vol. 66, Jul. 26, 2007, pp. 352-359.

Dancer, "How do we Assess Hospital Cleaning? A Proposal for Microbiological Standards for Surface Hygiene in Hospitals" Journal of Hospital Infection, vol. 56, 2004, pp. 10-15.

Zuhlsdorf et al., "Cleaning Efficacy of Nine Different Cleaners in a Washer-Disinfector Designed for Flexible Endoscopes," Journal of Hospital Infection, vol. 52, 2002, pp. 206-211.

Office Action from U.S. Appl. No. 12/766,714, dated Sep. 17, 2012, 28 pp.

Office Action from U.S. Appl. No. 13/369,056, dated Feb. 5, 2013, 16 pp.

Response to Office Action dated Dec. 6, 2013, from U.S. Appl. No. 12/787,064, filed Mar. 6, 2013, 7 pp.

Rifhat E. Malik et al., "Use of Audit Tools to Evaluate the Efficacy of Cleaning Systems in Hospitals," Am. J. Infect. Control, vol. 31, No. 3, p. 181-187 2003.

C. J. Griffith et al., "An Evaluation of Hospital Cleaning Regimes and Standards," J. Hosp. Infect., vol. 45, p. 19-28 2000.

Office Action from U.S. Appl. No. 12/766,714, dated Sep. 23, 2014, 20 pp.

Office Action from U.S. Appl. No. 14/136,889, dated Dec. 12, 2014, 21 pp.

Amendment in Response to Office Action mailed Sep. 23, 2014, from U.S. Appl. No. 12/766,714, filed Jan. 23, 2015, 10 pp.

* cited by examiner

STORAGE MAP 220

| What | Storage Conditions |
|---|---|
| Station and tools | Storage room or janitor closet. Dry room. Temp 50-100F |
| Proguard Quaternary Disinfectant | Storage/stock room or janitor closet. Dry room. Temp 55-85F |
| Textiles | In store room. Textiles must be dry (from dryer). In linen bags or on clean shelf. |
| Misc Station supplies (ie: trash bags, etc.) | Storage room or janitor closet. Dry room. Temp 50-100F |
| Johnny Mop | Store in use dilution disinfectant between shifts. If not to be used for multiple days soak in disinfecant for 10 min, rinse well, allow to dry. |

Fig. 5

VALIDATION PROCESSES - Patient Room Module — 230

| Validation Point | Process Step | Process Parameters | Monitoring Procedures | | | | Corrective Action |
|---|---|---|---|---|---|---|---|
| | | | What | How | Frequency | Who | |
| 1A | Dispense disinfectant | 1660ppm active quat in dispensed solution, 880ppm active quat in use solution post cloth/mop soak. | Quat titration | Procedure and TK 417 | Daily, weekly, biweekly, monthly, etc. | Protect Team member for pilot, EVS mgr or ICP for implementation | Follow trouble shooting procedure. If that does not work Contact Ecolab sales representative to adjust dispenser as needed |
| 1B | Dispense disinfectant | 1660ppm active quat in dispensed solution, 880ppm active quat in use solution post cloth/mop soak. | Quat test | Procedure and test strips | Daily, weekly, biweekly, monthly, etc. | Protect Team member for pilot, EVS mgr or ICP for implementation | Follow trouble shooting procedure. If that does not work Contact Ecolab sales representative to adjust dispenser as needed |
| 1C | Dispense Disinfectant | Proguard Quaternary Disinfectant Cleaner. | Verify correct product and sufficient product in concnetrate container by checking label and level of container | Visual | Prior to dispense | Worker filling station | Contact supervisor to obtain correct product and determine how incorrect product was delivered. Restock container per facility procedures to obtain more product. |
| 1D | Dispense Disinfectant | Dispense sufficient product to wet allocation of mops and cloths. | Count number of cloths/mops. Dispense sufficient product. | Visual use of fill lines on fill bucket | Every dispense | Worker filling station | Add more or pour out product if under/over filled. |
| 3A | Hand Hygiene pre-room clean | Waterless sanitizer use or hand washing for 15-20 sec. prior to donning gloves. | Hand hygiene compliance monitoring | Current facility procedures or ECL hand hygiene monitoring program. | Per procedure or monitoring program schedule. | EVS manager or ICP | Retraining |

Fig. 6A

| | | | | | | | |
|---|---|---|---|---|---|---|---|
| 3B | Hand Hygiene pre-room clean | Use of gloves. | PPE compliance monitoring | Current facility procedures or ECL hand hygiene monitoring program. | Per procedure or monitoring program schedule. | EVS manager or ICP | Retraining |
| 4 | Soiled Linen Laundry | Laundry procedure | Verification of laundry procedure | Verification method, e.g., photo- or chemi-luminescent indicators / ATP / cultures | Per laundry monitoring auditing schedule | Laundry manager or EVS manager w/ outside laundry if contracted. | Retraining |
| 5A | Bathroom cleaning | All surfaces contacted w/disinfectant impregnated cloth and remain wet for 10 min w/ disinfectant. | Surface cleaning monitoring | Verification method, e.g., photo- or chemi-luminescent indicators / ATP / cultures | Per monitoring / auditing schedule. | EVS manager or ICP | Retraining |
| 5B | Bathroom cleaning | All surfaces contacted w/disinfectant impregnated cloth and remain wet for 10 min w/ disinfectant. | Wet contact time | Monitor how long critical surfaces remain wet. | Per monitoring / auditing schedule. | EVS manager or ICP | Retraining |
| 6A | Room Cleaning | All surfaces contacted w/disinfectant impregnated cloth and remain wet for 10 min w/ disinfectant. | Surface cleaning monitoring | Verification method, e.g., photo- or chemi-luminescent indicators / ATP / cultures | Per monitoring / auditing schedule. | EVS manager or ICP | Retraining |
| 6B | Room Cleaning | All surfaces contacted w/disinfectant impregnated cloth and remain wet for 10 min w/ disinfectant. | Wet contact time | Monitor how long critical surfaces remain wet. | Per monitoring / auditing schedule. | EVS manager or ICP | Retraining |
| 7A | Hand Hygiene post-room clean | Waterless sanitizer use or hand washing for 15-20 sec. prior to donning gloves. | Hand hygiene compliance monitoring | Current facility procedures or ECL hand hygiene monitoring program. | Per procedure or monitoring program schedule. | EVS manager or ICP | |
| 7B | Hand Hygiene post-room clean | Use of gloves. | PPE compliance monitoring | Current facility procedures or ECL hand hygiene monitoring program. | Per procedure or monitoring program schedule. | EVS manager or ICP | Retraining |

Fig. 6B

| | | | | _230_ | | | |
|---|---|---|---|---|---|---|---|
| 8A | Station cleaning / storage | Station surfaces contacted w/ disinfectant impregnated cloth and remain wet for 10 min w/ disinfectant. | Surface cleaning monitoring | Verification method, e.g., photo- or chemi-luminescent indicators / ATP / cultures | Per monitoring / auditing schedule. | EVS manager or ICP | Retraining |
| 8B | Station cleaning / storage | Station surfaces contacted w/ disinfectant impregnated cloth and remain wet for 10 min w/ disinfectant. | Wet contact time | Monitor how long critical surfaces remain wet. | Per monitoring / auditing schedule. | EVS manager or ICP | Retraining |
| 9 | Soiled Textile Laundry | Prescribed wash procedure followed. | Verification of Proguard textile wash process | Audit | Weekly or monthly | Laundry manager or EVS manager w/ outside laundry if contracted. | Retraining |

Fig. 6C

ABC Hospital Summary

| | Baseline (Facility Wide) | Previous Period (4E) Baseline | Current Period (Post Implementation) |
|---|---|---|---|
| Continuous Improvement & Education<br>• Metrics<br>• Topics to Reinforce<br>• Best Practices | • Hygiene quiz results – 68% (4 employees)<br>• Topic: HAI's/HTO's | • HTO's, best practices, products & tools Launched Dec 2008<br>• 6 staff trained | • Re- Trained employees on floor 4E - 90% results |
| Operational Processes<br>• Cleaning Daily/Discharge<br>• Dispenser Accuracy<br>• Observations | • Discharge – 25.9 min<br>• Disinfectant dilution inaccurate<br>• Inadequate PPE usage | • Discharge – 23.6 min<br>• Mix of clean & dirty items on cart<br>• Inconsistent PPE usage | • Discharge time improved 23%<br>• 13 out of 13 tests – Accurate dilution for disinfectant |
| Hygiene Outcome Efficacy<br>• Marking Solution<br>• Cultures - Future | • Overall 49.5%<br>• Room 55.0%<br>• Bath 44.0% | • Gel Overall 69.3%<br>• Room 73.1%<br>• Bath 65.3%<br>• Cultures Overall 72.3% | • Gel Overall 83.4%<br>• Room 87.4%<br>• Bath 79.5%<br>• Cultures Overall 78.1% |
| Satisfaction<br>• Patient<br>• Staff | | • Patient Sat = 4.5 out of 5<br>• Staff – likes their job<br>• Staff rates their job important | • Patient Sat fell to 4 |

• = Baseline • = Critical • = Monitor • = Good

Fig. 8A

ABC Hospital

Hygiene Outcomes – Marking Solution

Percent Time High Touch Objects are cleaned

| High Touch Object Cleaning Gel | Baseline (Facility Wide) | Last Period Audit (4E Baseline) | Current Period Audit (4E Post) | Current Period vs Baseline +/(-) |
|---|---|---|---|---|
| * Overall HTO Cleaning | 49.5% | 69.3% | 83.4% | +33.9% |
| Patient Room Cleaning | 55.0% | 73.1% | 87.4% | +32.4% |
| Bathroom Cleaning | 44.0% | 65.3% | 79.5% | +35.5% |
| Most Cleaned HTO | 80.0% - Toilet Seat | 86.3% - Tray Table | 97.8 - Call Button | +75.8% |
| Most Frequently Missed HTO | 16.0% - Bath Door | 36.2% - Bed Pan Cleaner | 60.4% - Room Door | +9.1% |
| % Time All HTO's Cleaned | 2.0% | 2.0 % | 12.2 % | +10.2% |

* National Average is 47%

New Targeting Methodology
- Pre-mark HTO prior to cleaning
- After cleaning, analyze each HTO to determine % of area cleaned.

Cleaning HTO's in patient room
- Paramount to providing Safe & Protected Environment for patient & healthcare workers
- Best practices focuses on cleaning these points to help improve patient safety & reduce risk of HAI's

Fig. 8B

ABC Hospital
Hygiene Outcomes – Marking Solution

Detail Analysis of Percent Time High Touch Objects cleaned

| High Touch Objects | | Baseline (Facility Wide) | Last Period (4E Baseline) | Current Period (4E Post) | % Change Current vs Baseline |
|---|---|---|---|---|---|
| Call Button | 1 | 57.7% | 71.2% | 97.8% | 40.1% |
| Tray Table | 2 | 61.5% | 86.3% | 95.8% | 34.3% |
| Toilet Seat | 3 | 80.0% | 85.7% | 93.9% | 13.9% |
| Telephone | 4 | 84.6% | 76.5% | 93.8% | 9.1% |
| Bathrom Door | 5 | 16.0% | 70.0% | 91.8% | 75.8% |
| Bed Side Table | 6 | 53.8% | 75.0% | 91.7% | 37.8% |
| Bed Rail | 7 | 44.0% | 76.9% | 85.1% | 41.1% |
| Sink | 8 | 52.0% | 81.6% | 79.6% | 27.6% |
| Toilet Hand Hold | 9 | 40.0% | 46.9% | 77.6% | 37.6% |
| Toilet Handle | 10 | 52.0% | 70.0% | 71.4% | 19.4% |
| Bed Pan Cleaner | 11 | 24.0% | 36.2% | 62.5% | 38.5% |
| Room Door | 12 | 22.7% | 52.9% | 60.4% | 37.7% |
| Total Bath | | 44.0% | 65.3% | 79.5% | 35.5% |
| Total Room | | 55.0% | 73.1% | 87.4% | 32.4% |
| Overall | | 49.5%* | 69.3% | 83.4% | 33.9% |

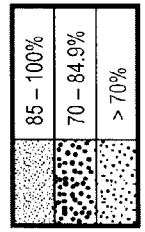

| | 85 – 100% |
| | 70 – 84.9% |
| | > 70% |

\* National Average is 47%

Fig. 8C

ABC Hospital
Hygiene Outcomes – Cultures

Detail Culture Analysis – Percent Occurrences Post Reading lower than Pre-Reading

| High Touch Object Cleaning – Total Aerobic Count Post Cleaning | Last Period ( 4E Base ) | Current Period (4E Post ) | Variance |
|---|---|---|---|
| Overall HTO Percent | 72.3% | 78.1% | +5.8% |
| Patient Room HTO Count | 79.7% | 83.8% | +4.1% |
| Bathroom HTO Count | 63.8% | 71.6% | +7.8% |
| HTO – Lowest Average Count | 33.3% Bath door knob | 53.8% Bath door knob | - |
| HTO – Highest Average Count | 100% Room door knob | 100% - Room door knob | - |

Culture Methodology
- Pre-cleaning cultures of HTO surfaces
- Post-cleaning cultures of HTO surfaces
- Microbiologist counted number of CFUs per swabbed area Cleaning HTO's in patient room
- Paramount to providing Safe & Protected Environment for patient & healthcare workers
- Best practice focuses on cleaning these points to help improve patient safety & reduce risk of HAI's

Fig. 8E

ABC Hospital
Hygiene Outcomes – Cultures

Detail cultures analysis – Percent occurrences post reading lower than pre-reading

| High Touch Objects | Last Period (4E Baseline) | Current Period (4E Post) | % Change Current vs Baseline |
|---|---|---|---|
| Call Button | 75.0% | 81.3% | 6.3% |
| Tray Table | 92.9% | 94.1% | 1.2% |
| Toilet Seat | 73.3% | 76.5% | 3.2% |
| Telephone | 69.2% | 73.3% | 4.1% |
| Bathroom Door | 33.3% | 53.8% | 20.5% |
| Bed Side Table | 78.6% | 81.3% | 2.7% |
| Bed Rail | 68.8% | 72.2% | 3.4% |
| Sink | 75.0% | 78.6% | 3.6% |
| Toilet Hand Hold | 62.5% | 64.7% | 2.2% |
| Toilet Handle | 70.0% | 81.3% | 11.3% |
| Bed Pan Cleaner | 57.1% | 72.7% | 15.6% |
| Room Door | 100.0% | 100.0% | 0.0% |
| | | | |
| Total Bath | 63.8% | 71.6% | 7.8% |
| Total Room | 79.7% | 83.8% | 4.1% |
| Overall | 72.3% | 78.1% | 5.8% |

Fig. 8F

ABC Hospital
Operational Efficiency

Discharge cleaning was reduced on average by 6.1 minutes

| Cleaning Description | Avg Time | Longest Time | Shortest Time | N |
|---|---|---|---|---|
| Discharge Cleaning (Baseline - Facility Wide) | 25.9 min | 34 min | 20 min | 7 |
| Discharge Cleaning (Last Period - 4E Baseline) | 23.6 min | 33 min. | 10 min | 30 |
| Discharge Cleaning (Current Period - 4E Post) | 17.5 min | 25 min. | 10 min | 26 |
| Variance in minutes (-)Favorable (+)Unfav. | -8.4 | -9 | -10 | |

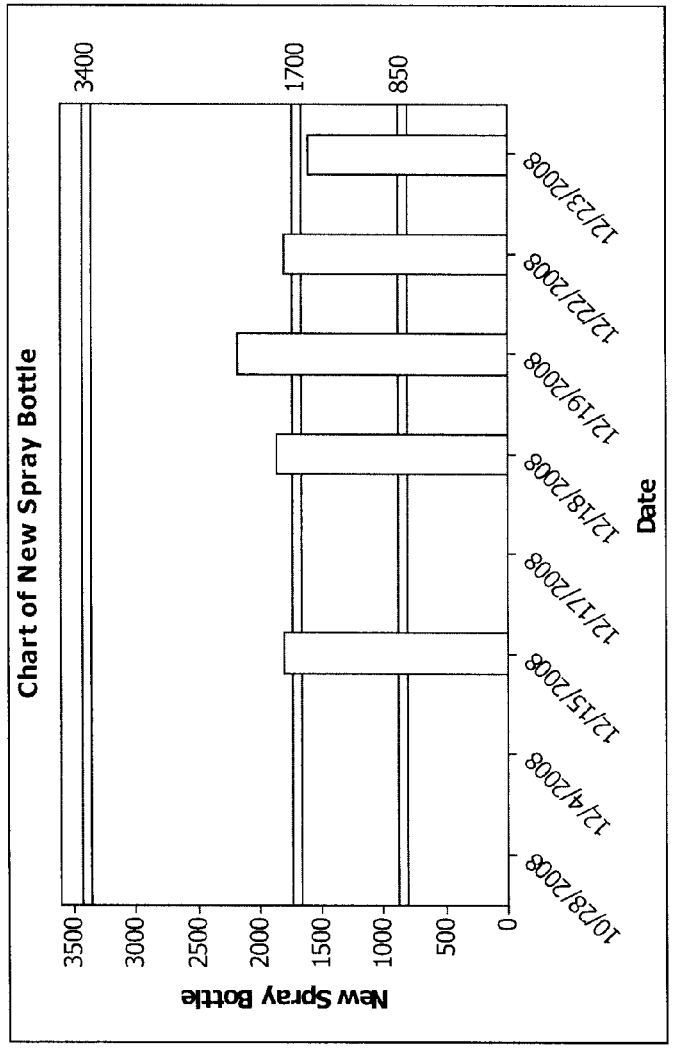

ABC Hospital
Operational Efficiency

Observations
Changing behavior takes right tools, time and reinforcement. Observation assists in determining where additional training its necessary.

Safety Recommendations:
- Perform regular audits to minimize labeling violations
- Train on Contact Isolation signage & product wipe usage (cases where wipes inappropriately used)
- Training to prevent food/drink on carts
- Provide 5S & visual mgmt techniques to organize carts to minimize cross contamination
- Cross contamination training (prevent redipping cloths)
- Train on proper use of PPE

Product Usage Recommendations:
- Train on appropriate disinfectant change out and importance
- Use mops according to training and icons

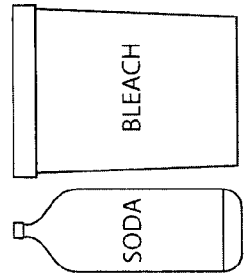

Fig. 8L

ABC Hospital Next Steps
Summary of Recommendations

NEXT STEPS

Continuous Improvement & Education
- Metrics
- Topics to Reinforce
- Best Practices

- Certify lead cleaners
  - Reinforce proper cleaning process (HTO's)
  - Introduce Hand Hygiene module

Operational Processes
- Cleaning Daily/Discharge
- Dispenser Accuracy
- Observations

- Reinforce rationale for appropriate PPE
  - Reinforce need to eliminate cross contamination
  - Train on proper chemical labelling

Hygiene Outcome Efficacy
- Marking Solution
- Cultures

- Set up training session to learn, practice, do using gel as training guide
  - Reinforce the importance of effectively cleaning HTO's

Satisfaction
- Patient
- Staff
- Nursing

- Provide housekeepers with training to help with patient interaction

VALIDATED HEALTHCARE CLEANING AND SANITIZING PRACTICES

CROSS REFERENCE TO RELATED APPLICATIONS

This application claims the benefit of U.S. provisional Application Ser. No. 61/125,922 filed Apr. 30, 2008, the entire contents of which is incorporated herein by reference.

TECHNICAL FIELD

The invention relates to cleaning and sanitizing practices at a hospital or other healthcare facility.

BACKGROUND

Despite improvements in hand hygiene, stricter compliance requirements, and efforts to optimize isolation practices, hospitals and other healthcare facilities are losing the war on nosocomial or Hospital Acquired Infections (HAIs). A hospital acquired infection is an infection acquired in a hospital or other healthcare facility by a patient admitted for some reason other than that specific infection. Hospital acquired infections may include infections appearing 48 hours or more after hospital admission or within 30 days after discharge. They may also include infections due to transmission from colonized healthcare workers, or occupational exposure to infection among staff of the facility. Although the majority of hospital acquired infections are preventable, sadly their incidence has only increased.

Hospital acquired infections have become more rampant as antibiotic resistance spreads. Many factors contribute to the increased incidence of hospital acquired infections among hospital patients. For example, hospitals house large numbers of people who are sick and therefore have weakened immune systems. Medical staff move from patient to patient and see many patients a day, providing a way for pathogens to spread. Research indicates that hand hygiene practices are followed only 40% of the time by healthcare workers, even after exhaustive process improvements and training efforts. Many medical procedures, such as surgery, injections and other invasive procedures bypass the body's natural protective barriers, providing entry points for pathogens. The wide-spread use of antibiotics has contributed to the emergence of resistant strains of microorganisms in healthcare facilities and well as in the community.

Nearly ¾ of surfaces in patient rooms are contaminated even after housekeeping has been completed. Many high touch objects in the patient room, such as doorknobs, bedrails, telephone, etc. are continuously re-contaminated. Patients and healthcare workers are thus exposed to many sources for potential pathogen transmission within a hospital room.

In addition, between 70% and 90% of incoming patients carrying Methicillin-Resistant *Staphylococcus aureus* (MRSA) or Vanocomycin-Resistant Enterococci (VRE) are never identified and isolated. Many hospitals are unaware that MRSA lingers on patient room surfaces long after the colonized patient is discharged. Doctors and nurses carry MRSA on their lab coats and uniforms 65% of the time, potentially passing this organism to other patients or the environment.

It has been estimated that 1 out of every 20 patients contract hospital acquired infections. This translates to nearly 2,000,000 patients each year. By 1995, deaths from documented hospital acquired infections had escalated to almost 90,000 per year for an average of 345 per hospital. The costs associated with hospital acquired infections are significant. The cost to treat hospital acquired infections has been estimated to reach $30 to $50 billion per year. The average additional hospital costs for a patient contracting a hospital acquired infection is $15,275.

Although certain individuals, such as the critically ill, the elderly, young children and those with compromised immune systems are at greater risk, no patient is immune from the risk of acquiring an infection during a doctor visit or hospital stay.

SUMMARY

In general, the invention relates to a comprehensive and systematic approach to cleaning and sanitizing practices at a hospital or other healthcare facility.

In one embodiment, the invention is direct to a system comprising a server computer that receives collected data from a healthcare facility, the collected data based on monitored validation points within a plurality of validation processes for the healthcare facility, a database coupled to the server computer that stores the collected data from the healthcare facility in association with hospital data that uniquely identifies the healthcare facility; the database further storing module data that defines modules within the healthcare facility and process map data that defines at least one validation process for each module within the healthcare facility, an analysis application resident on the server computer that analyzes the collected data and generates therefrom validation data indicative of cleanliness of the one or more healthcare facilities, and a reporting application resident on the server computer that generates reports that characterize the cleanliness of the healthcare facility based on the collected data, the validation data, the hospital data and the module data.

In another embodiment, the invention is directed to a method comprising identifying contamination vectors of hospital acquired infections within a healthcare facility, defining a plurality of modules within the healthcare facility, each module associated with a physical area within the healthcare facility or with a function performed within the healthcare facility, associating each of the plurality of modules with a different one of a plurality of cleaning process maps, monitoring validation points specified in one or more of the cleaning process maps, and verifying whether process parameters associated with each monitored validation point are satisfied.

The method may further include defining one or more of a patient room module, a critical care area module, a central sterile processing module, an operating room module, an emergency room module, a physical therapy module, a food service module, a public bathroom module, a procedure room module or a laundry area module. The method may further include defining one or more of a patient skincare module, a wound cleansing module, or a hand hygiene module. The method may further include correlating each of the plurality of modules with one or more of the contamination vectors. The method may further include generating one of the plurality of cleaning process maps based on the associated module and the contamination vectors correlated with the associated module. The method may further include training staff of the healthcare facility regarding the cleaning process maps. The method may further include re-training staff of the healthcare facility when the whether process parameters associated with certain of the monitored validation point are not satisfied. The method may further include generating validation data based on whether the process parameters associated with each monitored validation point are satisfied. The method may further include generating reports based on the validation data. In another embodiment, the invention is directed to a computer-readable medium comprising instructions that upon execution in a computer of a validated hospital cleaning processing system cause the computer to receive collected data from a healthcare facility, the collected data based on monitored validation points within a plurality of validation processes for the healthcare facility, store the collected data from the healthcare facility in association with hospital data that uniquely identifies the healthcare facility, store module data that defines modules within the healthcare facility, store process map data that defines at least one validation process for each module within the healthcare facility, analyze the collected data with respect to the process map data and generate therefrom validation data indicative of cleanliness of the one or more healthcare facilities, and generate at least one report that characterizes the cleanliness of the healthcare facility based on the collected data, the validation data, the hospital data and the module data.

The details of one or more embodiments of the invention are set forth in the accompanying drawings and the description below. Other features and advantages of the invention will be apparent from the description and drawings, and from the claims.

BRIEF DESCRIPTION OF DRAWINGS

FIG. 5 is a flow chart illustrating an example storage process map for the patient room module.

FIGS. 6A-6C are a chart illustrating example validation processes for the patient room module.

FIGS. 8A-8M show example reports that may be generated by reporting module 230 for the patient room module.

DETAILED DESCRIPTION

In general, the invention relates to comprehensive and systematic approach to cleaning and sanitizing practices at a hospital or other healthcare facility. A validated hospital cleaning process identifies hospital vectors of contamination; that is, possible sources through which hospital acquired infections (HAIs) may be spread. The validated process defines a plurality of modules within a hospital or other healthcare facility, each having an associated cleaning process map designed to meet the particular cleaning and/or sanitizing needs and challenges faced by that module. The cleaning process map for each module may be based, for example, on scientifically validated best practices of clearly defined cleaning processes. Various stages of the cleaning process map include validation points, at which certain parameters designed to ensure proper cleaning and/or sanitizing of the module are verified.

The validated hospital cleaning process may address clinical and cleaning procedures across many fronts within the hospital. The validated process may include some or all of the following: objective assessments, audits and measures; data collection, hazard analysis and critical control point identification; efficient and effective processes and protocols; training and interventions that change behaviors; consistent, automated and invisible monitoring; innovative products and technologies; clinical experts and personalized support services; quality assurance practices; implementation of best practices; and cleaning through clinical improvements that may reduce the incidence of HAIs.

Figure 1:
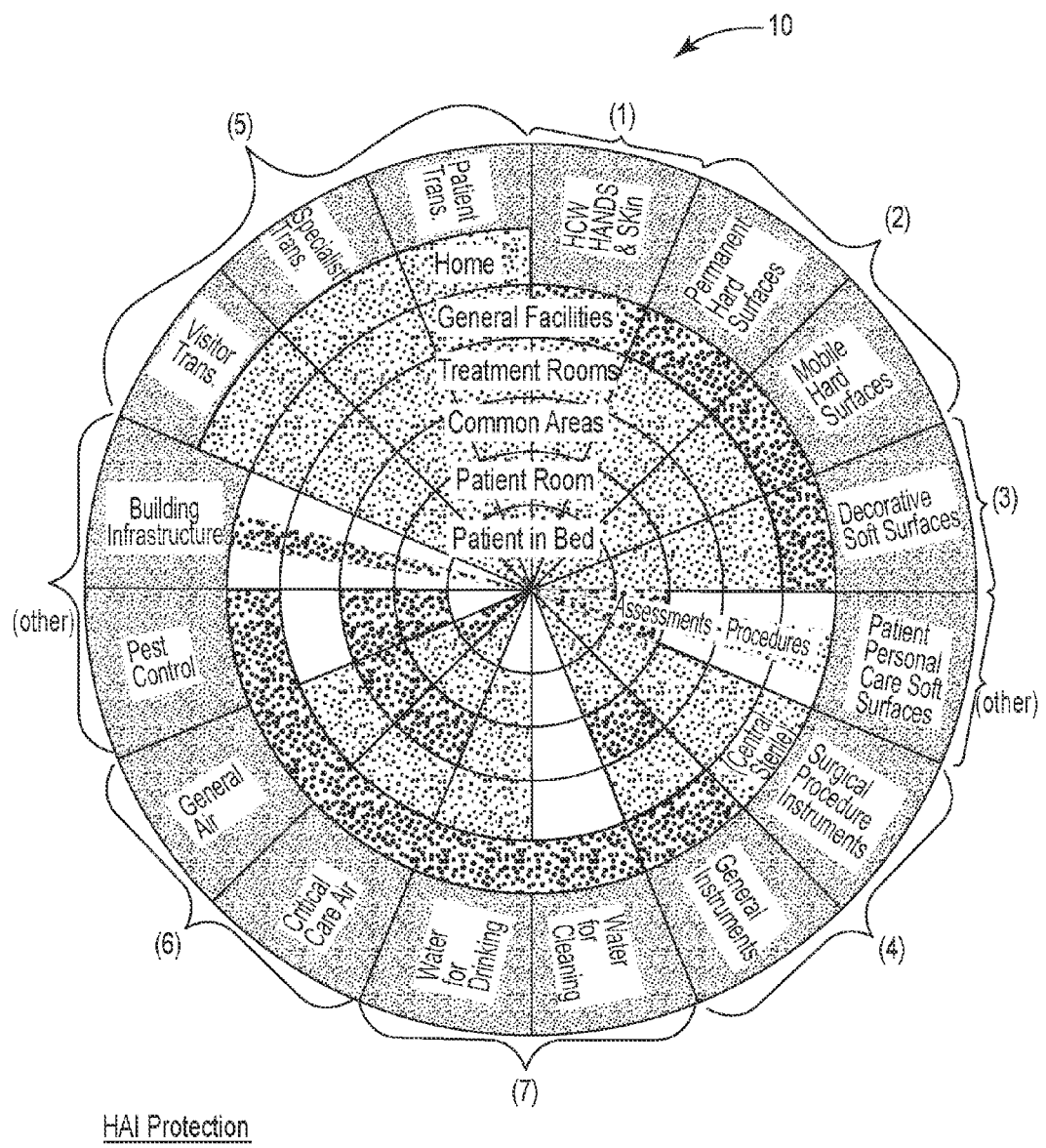
FIG. 1 is a diagram illustrating a vector wheel that describes hospital contamination vectors from a patient-centered perspective.

FIG. 1 is a diagram illustrating a vector wheel that describes hospital contamination vectors from a patient-centered perspective. At the center of the vector wheel is the patient. Moving from the center toward the outside of the vector wheel moves from a patient's immediate surroundings (e.g., patient to patient bed to patient room) into areas of a hospital that are increasingly shared by other patients, healthcare workers and/or the public. The vector wheel of FIG. 1, for example, moves from the patient at the center to the patient bed, patient room, common areas (such as nursing stations), treatment rooms (such as radiology or physical therapy), general facilities (such as waiting rooms, cafeterias, hallways, etc.) and finally to the patient's home and the world at large.

The vector wheel also illustrates the contamination vectors within a hospital or other healthcare facility that may be identified by the validated process of the present invention. The contamination vectors are represented as "slices" on the vector wheel and may include, in no particular order:

(1) Skin: healthcare worker hand hygiene and skincare (2) Hard surfaces: Permanent (bedrails, handles, floors, walls, etc.); mobile (carts, IV stands, wheelchairs, etc.)

(3) Soft surfaces: decorative and infrequently cleaned (partition curtains, drapes, carpet, wallpaper, etc.)

(4) Instruments: surgical procedure instruments; diagnostic procedure instruments (endoscopes, etc.), general instruments (stethoscopes, thermometers, etc.)

(5) Human transmission: patients, visitors & non-healthcare workers, healthcare workers & specialists. This may also be expanded to include service and therapy animals.

(6) Air quality: critical patient care and general, special considerations for construction and renovation (7) Water quality: patient care and contact, cleaning and/or sanitation (other) Building Infrastructure & Construction: mold and contaminates in walls, ducts, etc.; Pest Control; Patient Personal Care Soft Surfaces: linens, towels, gowns, etc.

Different areas of the hospital may require different levels of cleaning and/or sanitization. These may be classified, for example, as "clinical" and "clean." The vector wheel of FIG. 1 indicates an example distribution of areas within a healthcare facility that may be designated as clinical or clean. For example, "clinical" may be defined as an area where antimicrobial products such as EPA registered disinfectants or antimicrobial skin care products such as surgical scrubs or healthcare personnel hand washes should be used. "Clean" may be defined as areas where general purpose cleaning products and hand soaps may be used. Example "clean" areas on the vector map are shaded a dark gray while example "clinical" areas are shaded lighter gray.

Other areas on the vector wheel of FIG. 1 may require quality assurance practices. For example, hand hygiene compliance monitoring is important for healthcare workers, sterilization controls are important for surgical instruments and air quality and particle count is important for building infrastructure and construction.

Figure 2A:
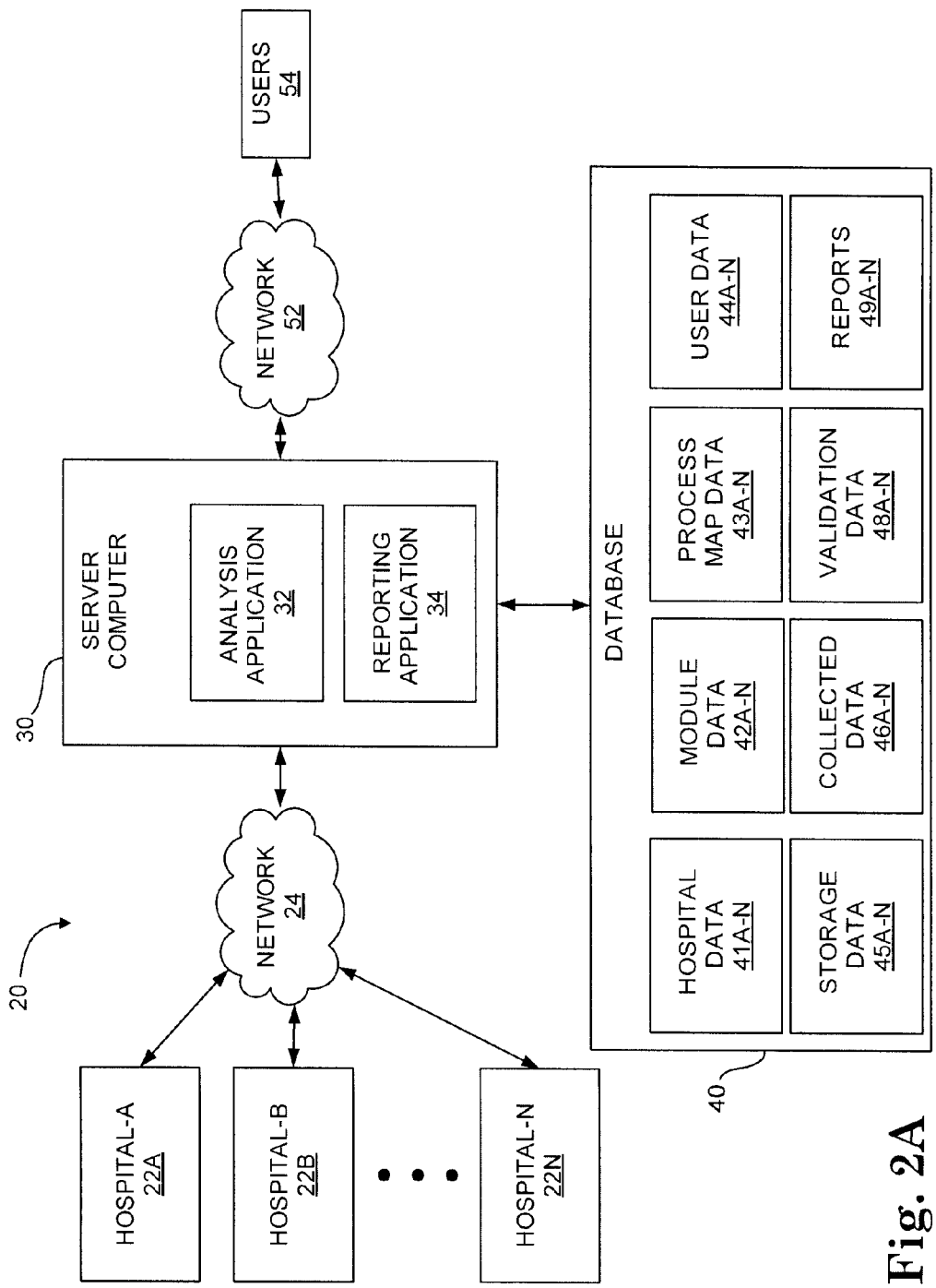
FIG. 2A is a block diagram illustrating an example environment within which the validated hospital cleaning system may be used.

FIG. 2A is a block diagram illustrating an example communications environment 20 within which the validated hospital cleaning system of the present invention may be used. One or more hospitals or other healthcare facilities 22A-22N are coupled via a network 24 to a server computer 30. Network 24 may be, for example, a dial-up connection, a local area network (LAN), wide area network (WAN), the internet, etc. The connection may be wired or wireless. Server computer 30 is coupled to a local server computer at each hospital 22A-22N via network 24 to receive data related to the validated hospital cleaning system that is stored on local storage media at each hospital. Server computer 30 may also send commands, instructions, software updates, etc. to each hospital via network 24. Server computer 30 may receive data or otherwise communicate with the hospitals on a periodic basis, in real-time, upon request of server computer 30, or at any other appropriate time.

The data received from hospitals 22A-22N, as well as other data associated with the operation of the validated hospital cleaning system, may be stored on a database 40. Database 40 may store, for example, hospital data 42A-42N associated with each of the hospitals 22A-22N, respectively; module data 43A-43N associated with each of the hospitals 22A-22N, respectively; process map data 43A-43N associated with each of the hospitals 22A-22N, respectively; user data 43A-43N associated with each of the hospitals 22A-22N, respectively; storage data 43A-43N associated with each of the hospitals 22A-22N, respectively; validation data 43A-43N associated with each of the hospitals 22A-22N, respectively; and collected data 43A-43N associated with each of the hospitals 22A-22N, respectively.

Hospital data 41A-41N may include data that uniquely identifies or is associated with the respective hospital or other healthcare facility 22A-22N. As such, hospital data 41A-41N may include, for example, hospital identification information, employee information, date and time stamps, caregiver identification, visitor identification and additional information relating to other aspects of the corporation or operation and other information specific to each individual hospital 22A-22N.

Module data 42A-42N may include, for example, module identification information for each module in the respective hospital 22A-22N. Modules may be physical modules associated with physical areas of hospital or may be functional modules associated with functions carried out within a hospital. Physical modules may include, for example, patient rooms, critical care areas, central sterile processing, operating rooms, food service, bathrooms, laundry rooms, floors, etc. Functional modules may include, for example, patient skincare, wound cleansing, hand hygiene, etc. Because each hospital or healthcare facility may perform different functions and have different physical areas within the healthcare facility, module data 42A-42N may be specific to the respective healthcare facility 22A-22N.

Process map data 43A-43N may include, for example, information that addresses the cleaning and/or sanitizing requirements for each module within the respective hospital 22A-22N. User data 44A-44N may include, for example, information concerning those persons or entities authorized to access the reports generated by the validated hospital cleaning system for the respective hospital 22A-22N. Storage data 45A-45N may include, for example, information that addresses proper storage and validation processes for the equipment, tools, cleaning and/or sanitizing products associated with each module for the respective hospital 22A-22N. Collected data 46A-46N may include, for example, any data collected at the respective hospital 22A-22N relevant to the validated hospital cleaning system. Collected data 46A-46N may also include baseline data corresponding to the status of monitored validation points before implementation of the validated hospital cleaning system/method. Validation data 48A-48N may include, for example, the results of any analysis of collected data 46A-46N received from the respective hospital 22A-22N.

Server computer 30 includes an analysis application 32 that analyzes the collected data 46A-46N received from each of hospitals 22A-22N and stores the results for each hospital 22A-22N as validation data 48A-48N, respectively. A reporting application 34 generates a variety of reports that present the validation data generated by analysis application 34. Reporting application 34 may generate a variety of reports to provide users with both qualitative and quantitative data regarding the cleanliness of their hospital, and/or to compare data over time to determine whether improvement has occurred. Reporting application 34 may also users to benchmark multiple hospitals or other healthcare facilities. It may also be an assessment tool that is used post cleaning to assess the effectiveness of the use of the validated cleaning system/process and to determine whether the proper procedures are being followed.

Reports 49A-49N may be stored in database 40. Examples of the reports that may be generated by reporting application 34 are described with respect to FIGS. 8A-8M. Reports 49A-49N may be accessed by various authorized users 54 over network 52. Network 52 may be the same as network 24 (in the case of the internet, for example) or may be a different network.

Figure 2B:
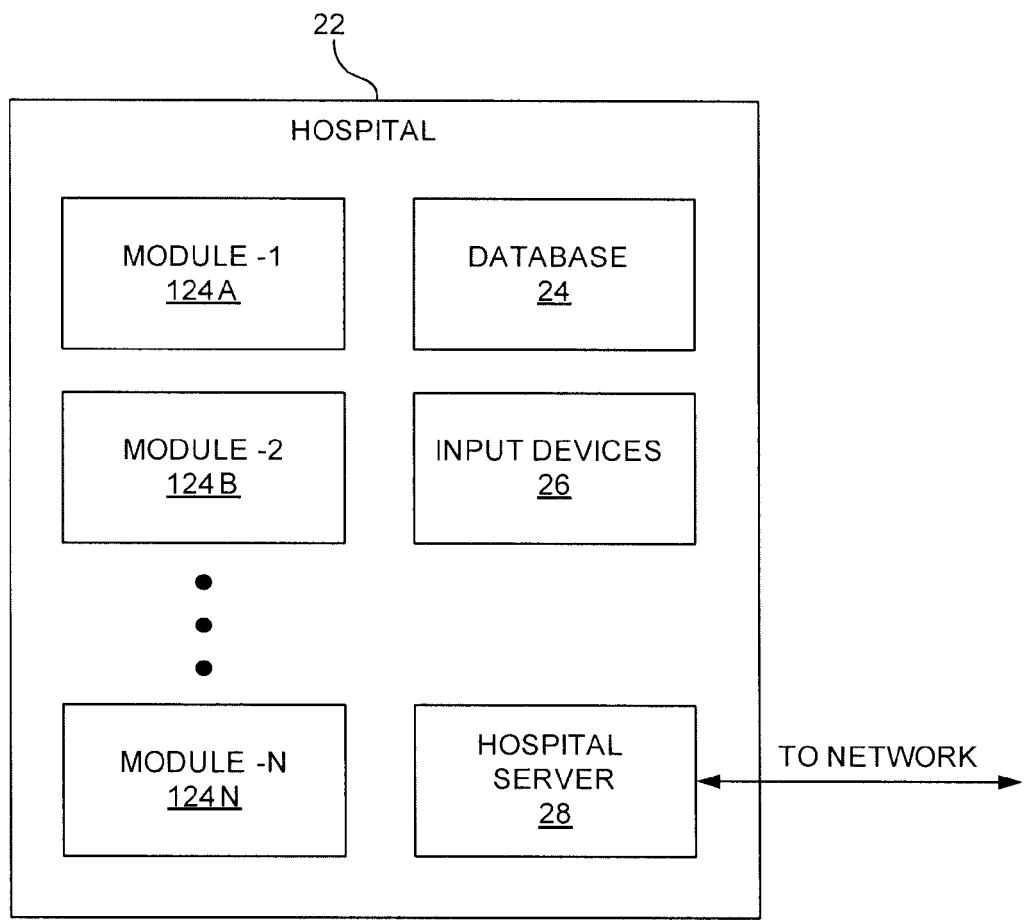
FIG. 2B is a block diagram illustrating an example hospital or other healthcare facility.

FIG. 2B is a block diagram illustrating an example hospital or other healthcare facility 22. Each hospital 22 includes a plurality of modules 124A-124N (hereinafter referred to generally as modules 124). As discussed above, modules 124 may be physical modules associated with physical areas of hospital or may be functional modules associated with functions carried out within a hospital. Each hospital 22 also includes a hospital server computer 28 that communicates with the server computer 30. Hospital 22 may also include a variety of input devices 26 into which collected data relevant to the validated hospital cleaning system is entered into the system. Input devices 26 may include, for example, networked computing stations, laptop computers, personal digital assistants, cell phones or any other means of entering collected data in electronic form. The collected data may be stored in a local hospital database 24. Alternatively, the collected data may be sent directly to server computer 30 to be stored in database 40.

In one embodiment, local hospital database 24 may store all of the data types described above with respect to database 40 associated with that particular hospital 22. Hospital server computer 28 (or other local computer) may also include local analysis and reporting applications such as those described above with respect to analysis and reporting applications 32 and 34. In that case, reports associated with that particular hospital may be generated and viewed locally, if desired. In another embodiment, all analysis and reporting functions are carried out remotely at server computer 30, and reports are viewed remotely over network 52, such as the internet. In other embodiments, some hospitals 22 may include local storage and/or analysis and reporting functions while other hospitals 22 rely on remote storage and/or analysis and reporting. Thus, although the general case of data being stored at the server database 40 and analysis/reporting being carried out by the server computer 30 is described herein, it shall be understood that these storage, analysis and reporting functions may also be carried out locally or at some other location, and that the invention is not limited in this respect.

Figure 2C:
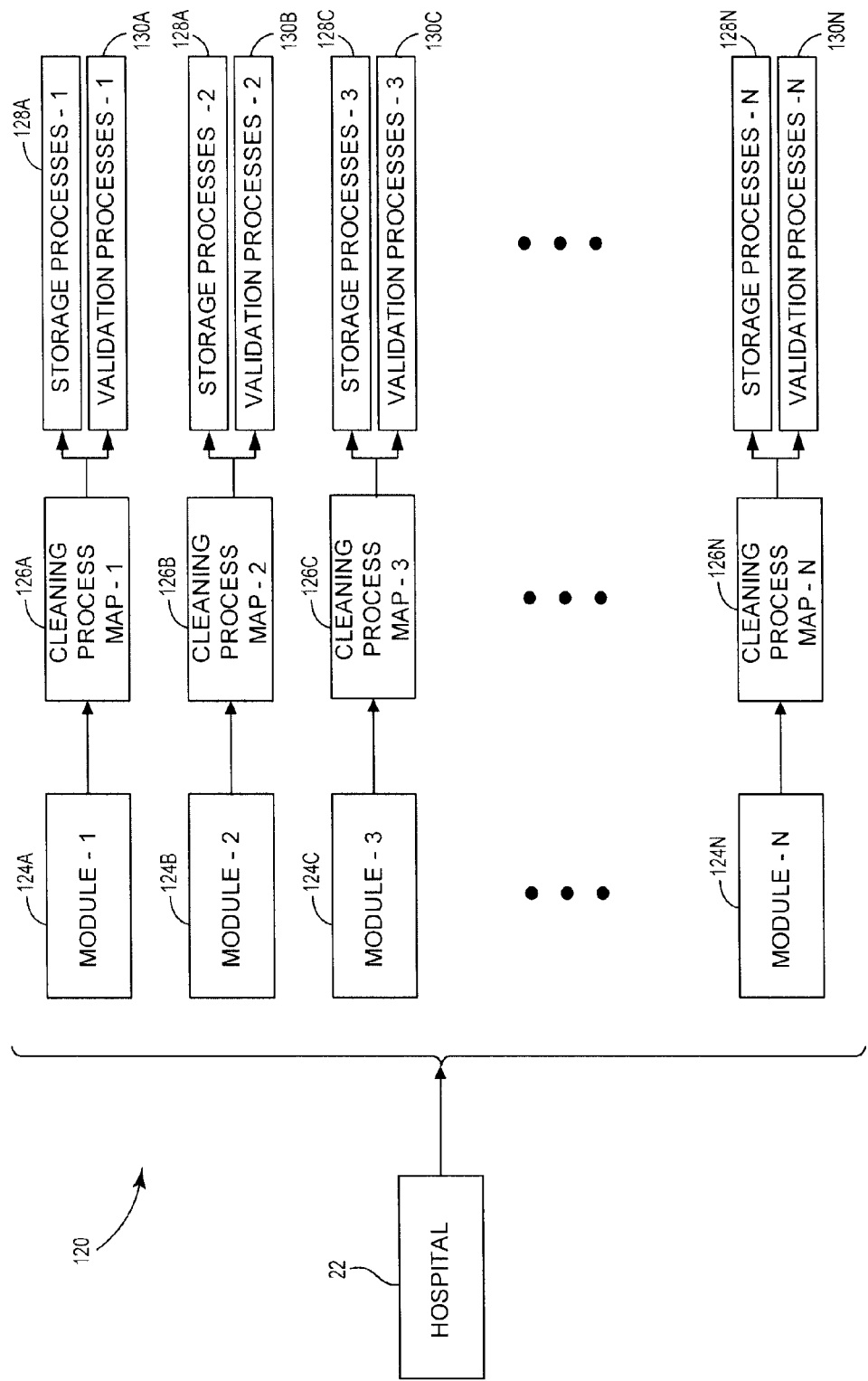
FIG. 2C is a block diagram illustrating an example breakdown of a hospital into modules and the processes associated with each module.

FIG. 2C is a block diagram illustrating modules 124A-124N within a hospital 22 or other healthcare facility and the processes associated with each module. The validated hospital cleaning process 120 of the present invention (hereinafter referred to generally as "validation process") defines a plurality of modules 124A-124N within a hospital. Modules 124A-124N may be physical modules associated with physical areas of hospital or may be functional modules associated with functions carried out within a hospital. Physical modules may include, for example, patient rooms, critical care areas, central sterile processing, operating rooms, food service, bathrooms, laundry rooms, floors, etc. Functional modules may include, for example, patient skincare, wound cleansing, hand hygiene, etc.

Each module 124A-124N is associated with a cleaning process map 126A-126N, respectively. The associated cleaning process map 126A-126N addresses the contamination vectors (FIG. 1) that are relevant to that module. For example, for the patient room cleaning module, the vectors addressed may include, among other things, skin (healthcare worker hand hygiene and skin care), hard surface (disinfection of mobile and permanent surfaces), soft surfaces (cleaning and where appropriate sanitation of privacy curtains), etc.

Each cleaning process map 126A-126N addresses the cleaning and/or sanitizing requirements of the associated module. For example, the patient room cleaning process map may include processes for stocking the patient room cleaning station, how cleaning personnel are notified of patient discharge, preparation of room for cleaning, removal of garbage, removal of linen, cleaning of bathroom, cleaning of the patient room, floor cleaning, and restocking of cleaning station, etc. The process map(s) associated with other module(s) within the hospital will include processes unique to that module aimed toward proper cleaning and/or sanitization practices and consideration of the relevant contamination vectors within that module.

Each cleaning process map 126A-126N lists all components and steps in the cleaning process. Validation points are inserted at certain identified process steps in the process flow map for each module. The validation points are inserted for identified process steps which, if not performed properly, there is a potential increased incidence of an unclean room or HAI infection risk.

As is also shown in FIG. 2C, each cleaning process map 126A-126N is associated with storage processes 128A-128N and validation processes 130A-130N, respectively. Storage processes 128A-128N refer to the proper storage conditions for the equipment, tools, cleaning and/or sanitizing products associated with each module. For example, the storage process map for the patient room module may include the proper storage conditions for the patient room cleaning station and tools, quaternary disinfectant (quat), textiles, miscellaneous station supplies such as trash bags, etc., a toilet bowl brush, etc. The storage process map(s) associated with other module(s) within the hospital will include product/equipment storage processes unique to that module aimed toward proper cleaning and/or sanitization practices within that module.

The validation processes 130A-130N refer to processes carried out at specified critical control points during the cleaning process, herein referred to as validation points. These validation points are identified points during the cleaning process at which certain parameters that may ensure proper cleaning and/or sanitizing of the module are verified.

For example, the validation processes for the patient room module may include verifying that a dispensed disinfectant solution contains the proper concentration of active ingredient, verifying that certain hard surfaces are contacted with a disinfectant impregnated cloth for a predetermined period of time, use of waterless sanitizer during hand washing, washing of hands both pre- and post-room cleaning, station cleaning, etc. The validation process map(s) associated with other module(s) within the hospital will include validation processes unique to that module aimed toward proper cleaning and/or sanitization practices within that module.

The validation processes for each module may be developed using the following considerations. Proper cleaning requires effective products and practices, training and monitoring. Effective disinfection and sterilization requires proper cleaning and storing, effective products and practices, training, compliance and monitoring. Clinical solutions require proper cleaning, effective disinfection and sterilization, innovative products and technology, process improvements, data analysis, training, compliance and monitoring. Depending upon the module and the vectors affecting that module, any number of these considerations may affect the resulting validation process.

Figure 3:
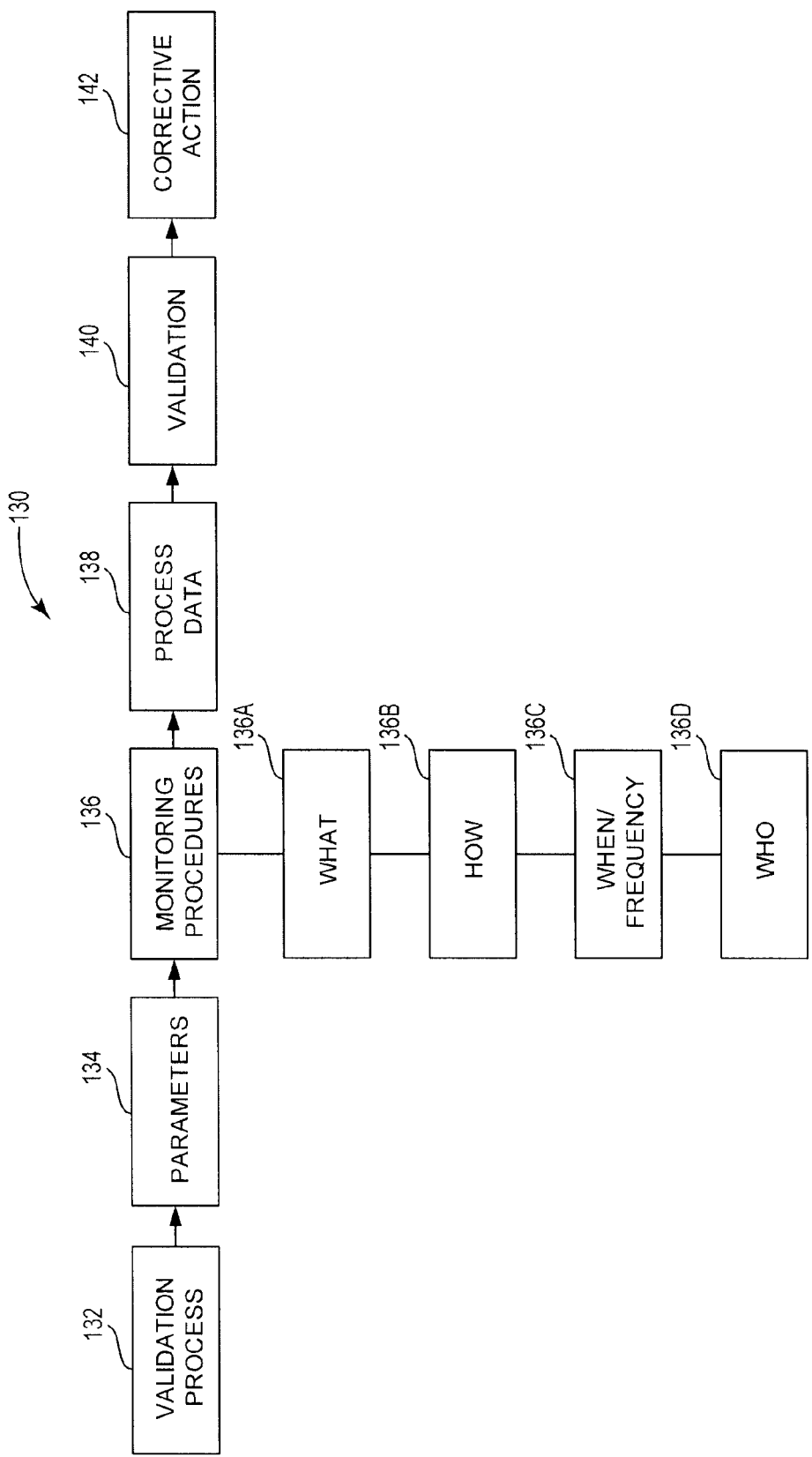
FIG. 3 is a block diagram illustrating an example of a generalized validation process flow map.

FIG. 3 is a block diagram illustrating an example of a generalized validation process flow map 130. Each validation point in a cleaning process map will include its own associated validation process flow map 130. The validation process flow map 130 identifies parameters 134 that must be met during the validation process. For example, the patient room module cleaning process flow map may include a validation point when disinfectant is dispensed. The parameters to be met may include, for example, requirements that the concentration of active ingredient within the disinfectant falls within certain limits, that proper disinfectant concentration is delivered to the relevant surfaces, elimination of cross contamination, etc. Other validation points may include parameters relevant to that particular point in the module cleaning/sanitizing process.

The process flow map also includes monitoring procedures 136 which may be used to verify that the parameters are satisfied. These monitoring procedures 136 may include a definition of one or more of the following:

What (136A): the monitoring procedure(s) which may be used to determine whether the parameters are satisfied (e.g., active ingredient titration or test in the case of dispensing disinfectant).

How (136B): the test or verification procedure which may be used to determine whether the parameters are satisfied (e.g., definition of titration procedure or test, use of visual indicators, verification methods such as surface cultures, time-based monitoring, etc.)

Frequency (136C): how often should the monitoring procedure be performed (e.g., after each cleaning, daily, weekly, monthly, etc.)

Who (136D): who will perform the monitoring procedure (e.g., hospital environmental services manager, service technician, cleaning personnel, independent vendor, etc.)

For example, the monitoring procedures for the validation point when disinfectant is dispensed may include regular dispenser validations and laboratory dispenser reliability testing to ensure that the concentration of active ingredient within the disinfectant falls within certain limits, laboratory testing on microfiber or other cleaning cloths to ensure that proper disinfectant concentration is delivered to the relevant surfaces (in other words, ensuring that the cloths do not absorb too much of the disinfectant), use of color coded cloths, carts with designated "clean" and "dirty" areas, and single use mops to eliminate cross contamination.

The results of the monitoring procedure(s) 136 are referred to herein as collected data. The collected data may be stored on the local hospital database 24 (see FIG. 2B) until such time as it is to be sent to server computer 30 (see FIG. 2A). Once received by server computer 30, collected data from each hospital 46A-46N is stored on server database 40. Examples of collected data may include without limitation one or more of the following data types: titration or other test results; disinfectant/sanitizer or other chemical product concentrations; dispensed detergent amounts; dispensing times, dates, and sequences; water temperatures; autoclave temperatures; chemical product types; wet contact times; results of microbial cultures, including type and number of organisms in a sample; bioluminescence readings, protein detection, particle counts; and/or other information relevant to the monitoring procedures at each module.

As is further shown in FIG. 3, a validation procedure 140 is performed on the collected data to verify whether the parameters of the validation point were satisfied. The validation procedure is performed by an analysis application, such as analysis application 32 resident on server computer 30 (see FIG. 2A). In other examples, the local hospital server 28 (FIG. 2B) or other local hospital computer may include a local analysis application that performs the validation process 140. The validation procedure may include a comparison of the collected data with the predetermined parameters.

The results of the validation procedure is referred to herein as validation data. The validation data may be stored on the local hospital database for those installations where the local hospital server or other local hospital computer includes a local analysis application. Validation data 48A-48N for each hospital 22A-22N may also be stored on the server database 40 (see FIG. 2A).

If the analysis application 32 validation procedure indicates that the validation parameters were not satisfied, the validation process flow map may include a corrective action process 142. Corrective action 142 may include equipment troubleshooting, retraining of personnel in proper cleaning/sanitizing procedures, etc.

The validated hospital cleaning system/process may analyze the hospital data 41A-41N, module data 42A-42N, process map data 43A-43N, user data 44A-44N, storage data 45A-45N, collected data 46A-46N, and validation data 48A-48N either alone or in combination with each other to characterize cleanliness of the hospital or healthcare facility 22A-22N. The validated hospital cleaning system/process may also generate reports 49A-49N that present the data in various formats and present the analysis for review by a site manager, corporate or government entity or other body responsible for oversight of the healthcare facility or of the validated hospital cleaning process.

FIGS. 4A-4G are a flow chart illustrating an example validation process flow map for a patient room module. As shown in the symbol key (164) in FIG. 4A, the process flow map may include, for example, process main steps, process sub-steps, tool and item lists, options, tools or guides lists, identification of what to evaluate at particular steps, and validation points.

Figure 4A:
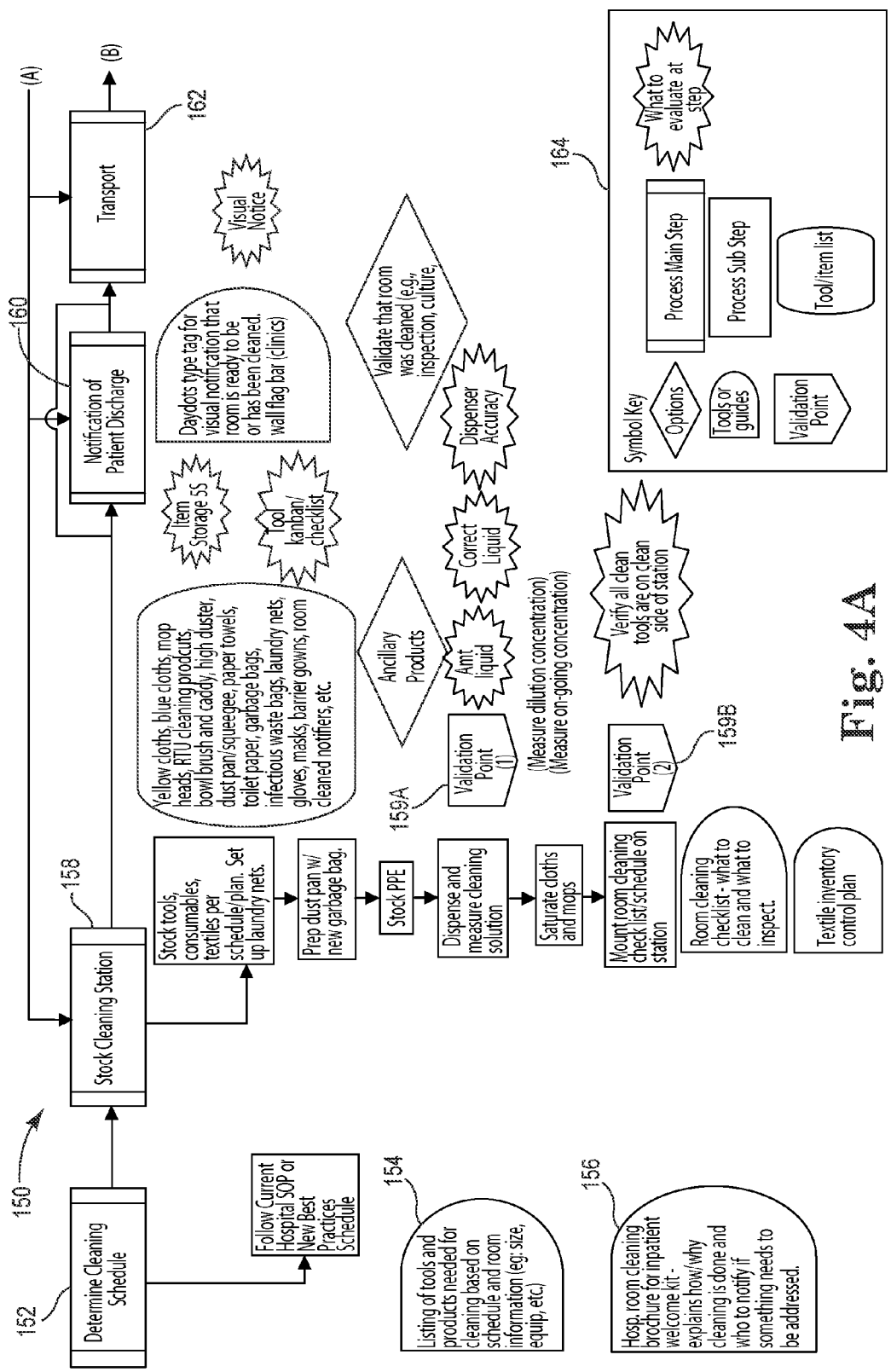
FIGS. 4A-4G are a flow chart illustrating an example validation process flow map for the patient room module.

FIG. 4A, shows an example of a "Determine Cleaning Schedule" main process step (152). This may be simply to follow the hospital's current cleaning practices or may be another cleaning schedule as determined by best practices or other means. A listing of tools and products (154) needed for cleaning based on the schedule and room information (e.g., size, equipment in room, furniture in room, etc.) may be included. A hospital room cleaning brochure/inpatient welcome kit (156) to be provided to each patient may also be included.

FIG. 4A also shows an example of a "Stock Cleaning Station" process step (158). This may include several sub-steps. The various tools, consumables, textiles, required during each scheduled cleaning may be stocked onto the cleaning station and laundry nets may be set up. A list/checklist of tools (see FIG. 4A) and other ancillary products may be provided.

The dust pan may be prepped with a new dust bag. Personal protective equipment (PPE), such as gloves, masks, eye-protection, gowns, etc. is stocked onto the cleaning station. The appropriate cleaning solutions are dispensed and measured. Cloths and mops are saturated with cleaning solution. A room cleaning checklist and/or schedule may be mounted onto the cleaning station. The room cleaning checklist may include a list of what to clean and what to inspect during the patient room cleaning process. A textile inventory control plan may also be in place to keep track of textiles (sheets, towels, gowns, etc.) going into or out of the patient room.

The portion of the patient room validation process shown in FIG. 4A includes two validation points; validation point (159A) occurs when the cleaning solution(s) are dispensed and measured. At this validation point, the relevant parameters of the cleaning solution(s), e.g., the amount of product dispensed, the type of product dispensed, the product concentration, and/or the dispenser accuracy may be monitored and, if the parameters are met, verified. Validation point (159B) occurs when the room cleaning checklist is mounted on the cleaning station. At this validation point, the cleaning personnel may verify that all tools/equipment are on the clean side of the cleaning station.

At main step "Notification of Patient Discharge" (160) includes some type of notice to cleaning personnel that a patient has been discharged. If the room is to be cleaned before a patient is discharged, this step may be skipped. The cleaning station is then transported to the patient room for cleaning (162).

Figure 4B:
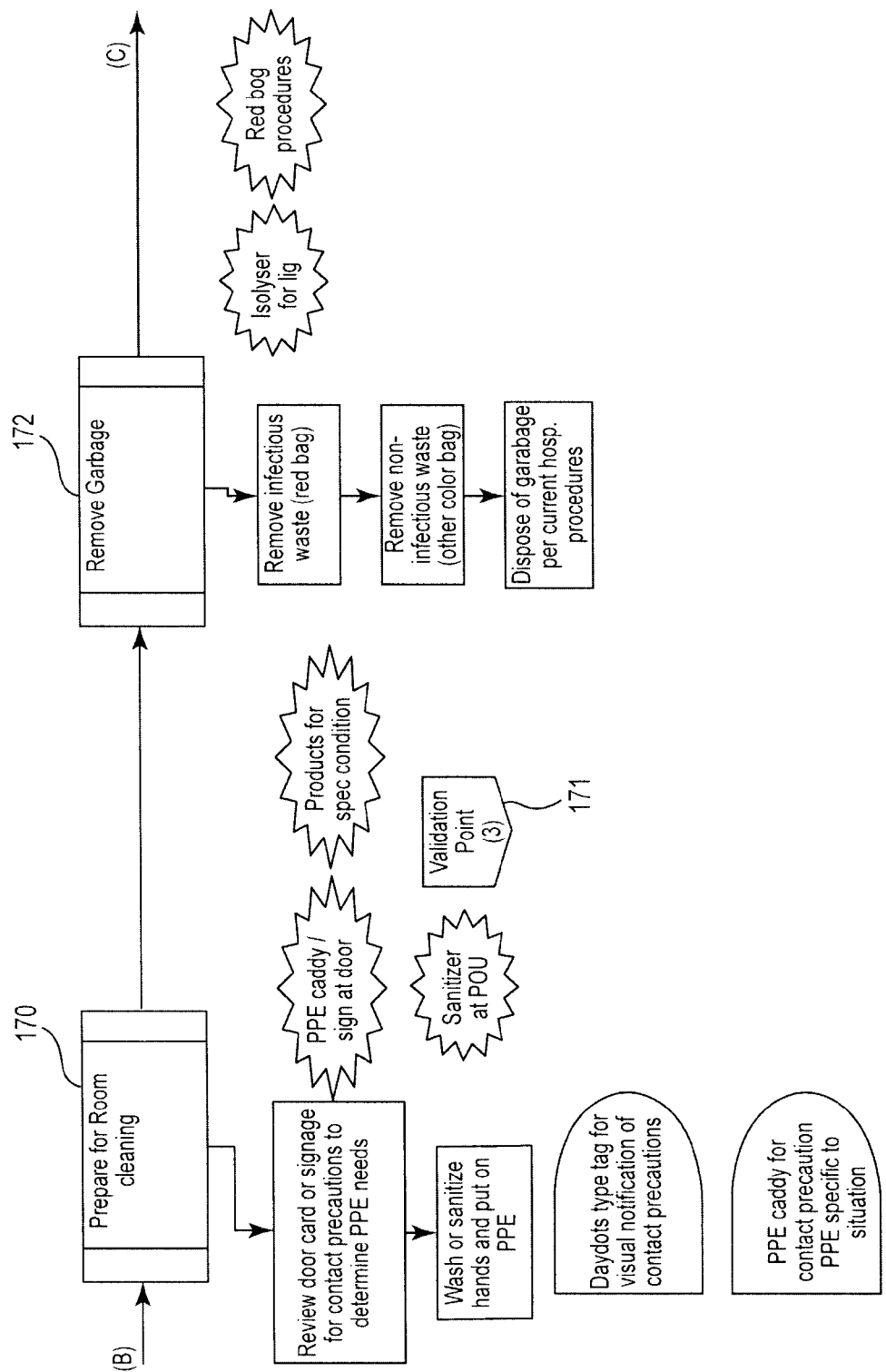

FIG. 4B shows an example of a "Prepare Room for Cleaning" main process step (170). This may include several sub-steps. For example, cleaning personnel may review a door card or signage for contact precautions to determine PPE needs. For example, cleaning personnel may be notified if a patient having certain conditions occupied or is currently occupying the room so that personal protective precautions may be taken. The "Prepare Room for Cleaning" process (170) may prompt cleaning personnel to wash and/or sanitize their hands and put on the relevant PPE. Validation point (171) occurs at this pre-room cleaning hand washing step.

FIG. 4B also shows an example of a "Remove Garbage" main process step (172). Main process step "Remove Garbage" may include removal of infectious waste, removal of non-infectious waste, and disposal of garbage per current hospital procedures or other best practices.

Figure 4C:
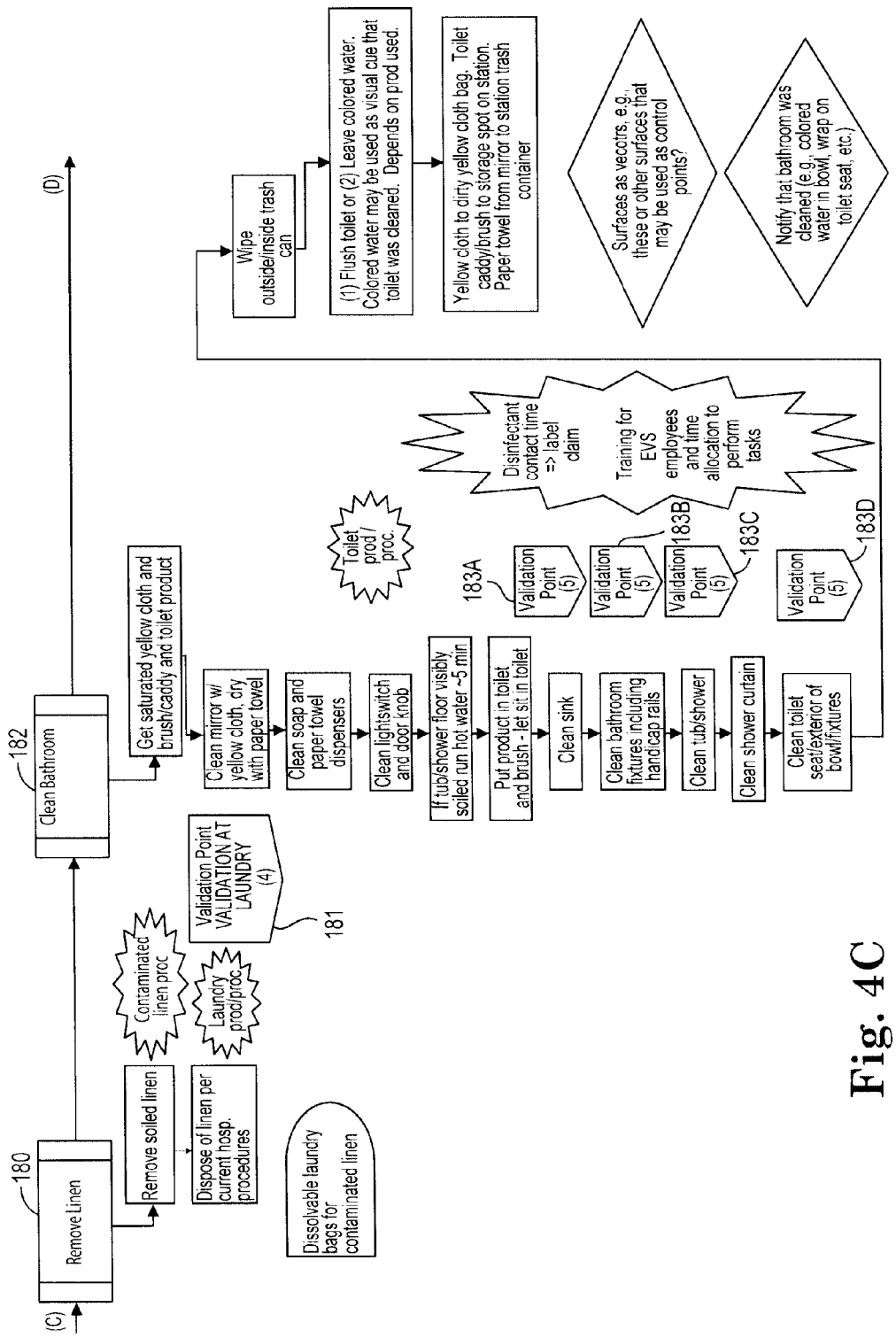

FIG. 4C shows an example of a "Remove Linen" main process step (180). Main process step "Remove Linen" may include removal of soiled linen and disposal of linen as per current hospital procedures or other best practices. Procedures for contaminated linen and/or other laundry protocols and procedures may also be included. Validation point (181) occurs at the laundry, where validation of various laundry parameters to ensure that laundry is properly cleaned and sanitized.

FIG. 4C also shows an example of a "Clean Bathroom" main process step (182). Main process step "Clean Bathroom" may include several sub-steps. The process may include getting a saturated cloth and brush/caddy and toilet product from the cleaning station, cleaning the mirror, cleaning soap and paper towel dispensers, and cleaning the light switch and the door knob. The cleaning product may also be sprayed or otherwise applied to the surfaces rather than using a saturated cloth. If the tub/shower is visibly dirty, the process may include running hot water for a predetermined period of time. The appropriate toilet cleaning/sanitizing product is placed in the toilet and left for a specified period of time. The sink, bathroom fixtures including handicap rails, tub/shower, shower curtain and toilet seat/bowl/exterior/fixtures are cleaned. Several critical control points, here referred to generally as validation points (183A-183D) may occur during the "Clean Bathroom" process step. These validation points may include validation of proper hard and/or soft surface cleaning procedures, such as wet contact time, culture results, photoluminescent or chemiluminescent indicators, etc.

The "Clean Bathroom" process step (182) may also include cleaning/wiping of the outside and/or inside of the bathroom trash can. The toilet may be flushed, or, in the alternative, the toilet may be left unflushed, thus leaving the colored water produced by the toilet cleaner present in the bowl as a visual indicator that the toilet has been cleaned. After cleaning the bathroom, the cloth used to clean the mirrors, etc. is placed in the dirty cloth bag. The toilet caddy/brush is returned to its storage spot on the cleaning station. The paper towel from the cleaning the mirror, etc. is placed in the trash. A notification that the bathroom was cleaned, such as colored water in the toilet bowl, wrap on toilet seat, etc. may also be included.

In addition, to the validation points (183A-183D) shown in FIG. 4C, other validation points associated with other surfaces that are now or in the future determined to be important contamination vectors may also be incorporated into the "Clean Bathroom" process step (or any other validation process associated with any of the modules, for that matter).

The "Clean Bathroom" process step (180) thus includes cleaning/wiping of some or all of a plurality of high touch points (HTP) (also referred to herein as high touch objects (HTO)). The high touch points for a bathroom may include, for example, the bathroom light switch, bathroom door knob, sink, toilet top, toilet handle, toilet hand hold/rails, bed pan cleaner, and/or any other physical item or area in a patient bathroom that may be frequently re-contaminated.

Figure 4D:
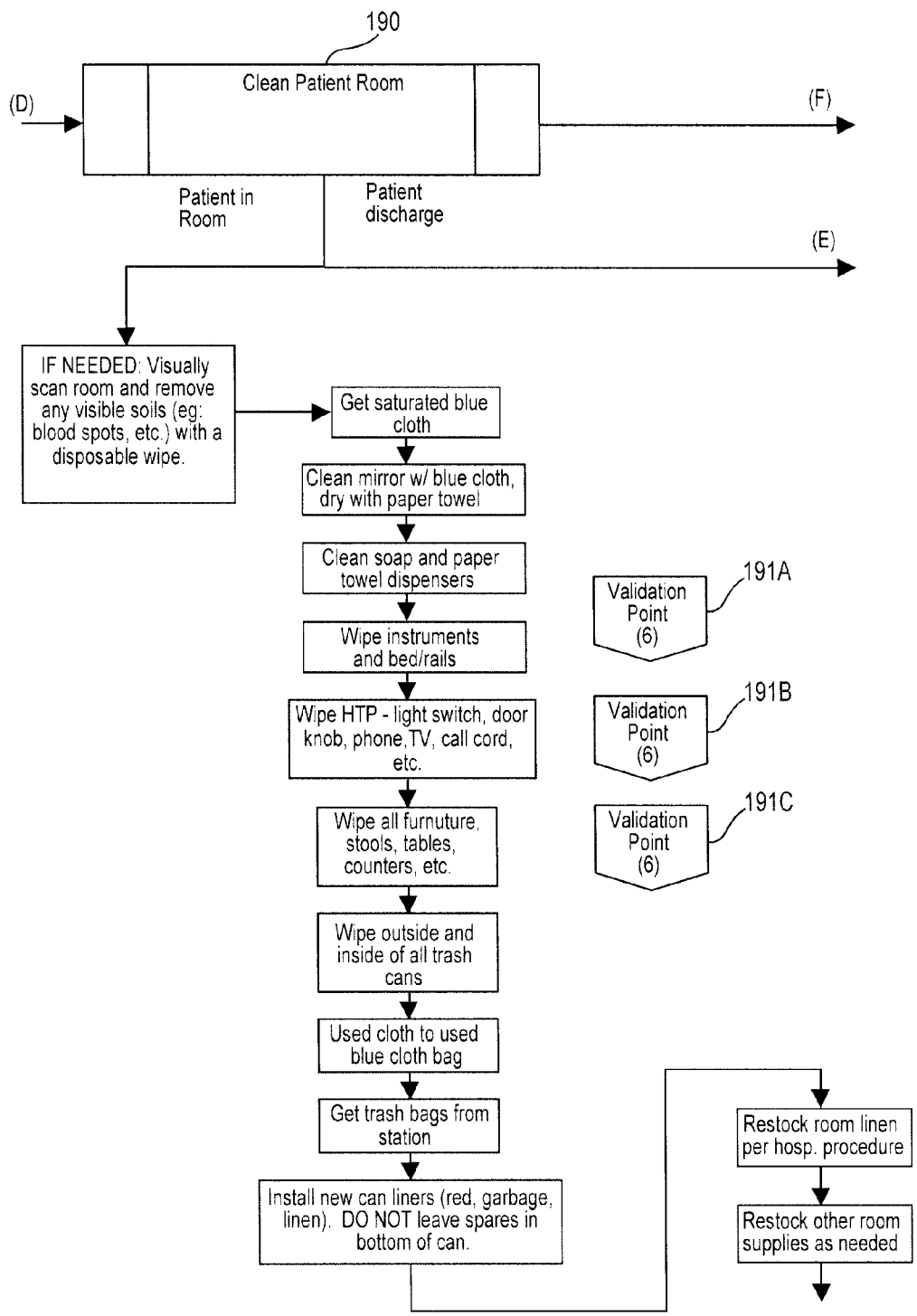

FIG. 4D shows an example of a "Clean Patient Room" main process step (190). This process step may diverge depending upon whether the patient still occupies the room (left branch) or whether the patient has been discharged (right branch). If the patient still occupies the room (regardless of whether the patient is physically present in the room at the time of cleaning) the process may include visually scanning the room and removing any visible soils, such as blood spots or other stains/soils, with a disposable wipe or other appropriate soil cleaning method. At this point the process may include getting a saturated cloth from the cleaning station, cleaning the mirror, soap and paper towel dispenser and wiping any instruments, the bed and the bed rails. Other cleaning methods, such as applying the cleaning/sanitizing product to the surfaces by spray or other means could also be used.

The "Clean Patient Room" process step (patient in room) may also include cleaning/wiping of some or all of a plurality of high touch points (HTP). The high touch points may include, for example, the light switch, door knob, telephone, TV, call box, tray table, bedside table, bedrails, and/or any other physical item or area in a patient room that may be frequently re-contaminated. The "Clean Patient Room" process step (patient in room) may also include wiping of all furniture including stools, tables, chairs, counters, etc.

Validation point(s) (191A-191C) occur during the "Clean Patient Room" process step. Here, validation of various cleaning procedures parameters to ensure that the patient room is properly cleaned and sanitized are monitored. For example, the validation point(s) (191A-191C) may require that all relevant surfaces are contacted with a disinfectant impregnated cloth and remain wet for at least 10 minutes with disinfectant. Monitoring may be accomplished via visual inspection of how long surfaces remain wet, photo- or chemiluminescent indicators, adenosine triphosphate (ATP), culture, etc., to ensure that proper cleaning/sanitizing procedures were adequately performed.

The "Clean Patient Room" process step (patient in room) may also include placing the used cloth(s) to the used cloth bag, getting trash bags from the cleaning station, installing new can liners (infectious waste can, used linen can, trash can, etc.), restocking room linens and other room supplies as needed, and other process steps necessary to prepare the room for another patient. Cloths for different areas or modules may be color coded, e.g., yellow cloths for bathroom, blue cloths for the patient room, etc., to reduce cross contamination between areas or modules.

Figure 4E:
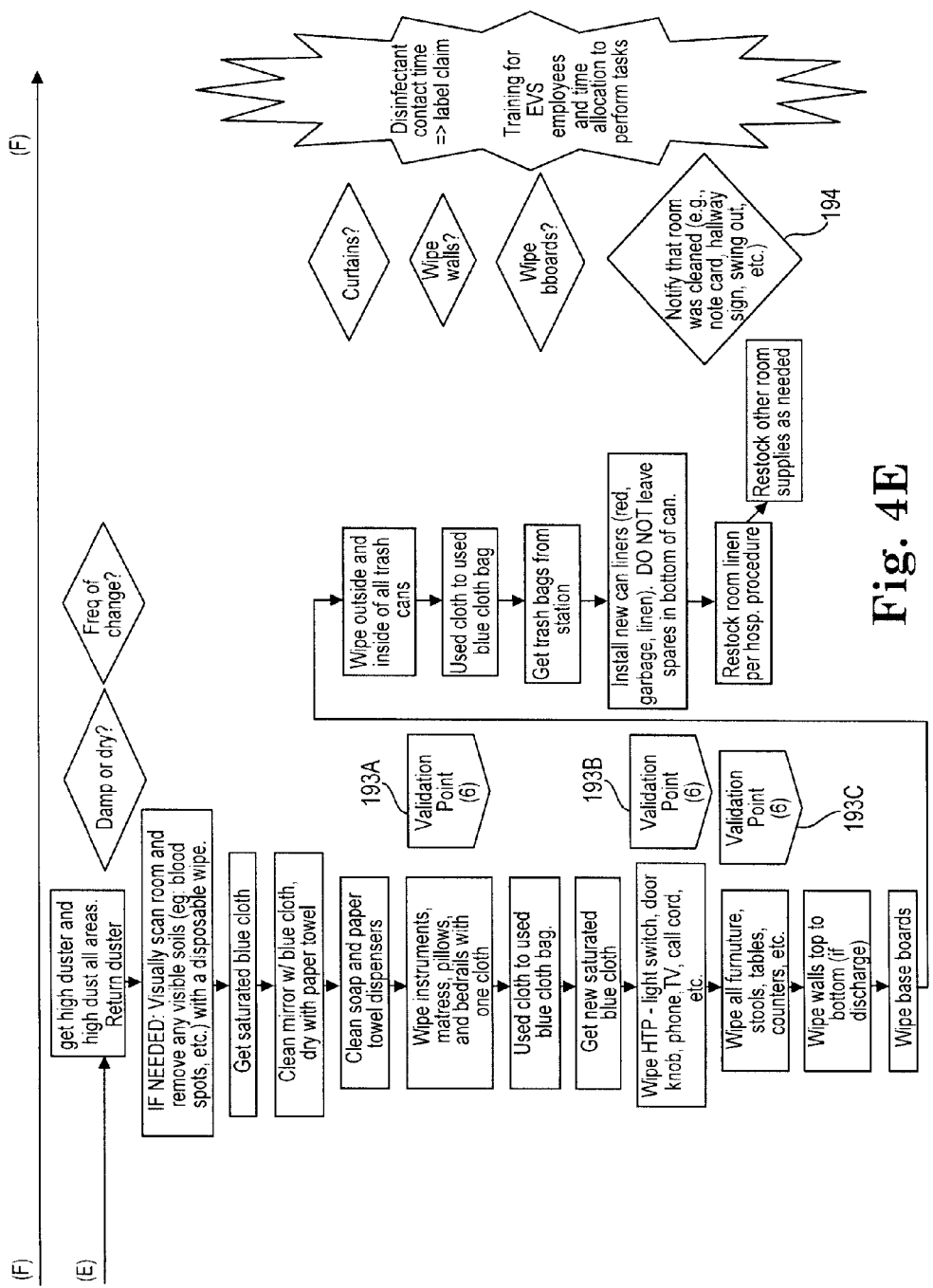

FIG. 4E shows an example of a patient discharged branch of a "Clean Patient Room" main process step. This branch includes many of the sub-steps as the patient in room branch shown in FIG. 4D. However, certain steps may be performed after the patient has been discharged that may be undesirable when the room is occupied by a patient, such as dusting of high surface areas (ceilings, ceiling light fixtures, fans, etc.) and the wiping of walls and baseboards. Validation point(s) (193A-193C) are monitored to ensure that the patient room is properly cleaned and sanitized.

The "Clean Patient Room" process may also include a notification that the patient room has been cleaned, such as a note card, hallway sign, swing out, etc. (194).

Figure 4F:
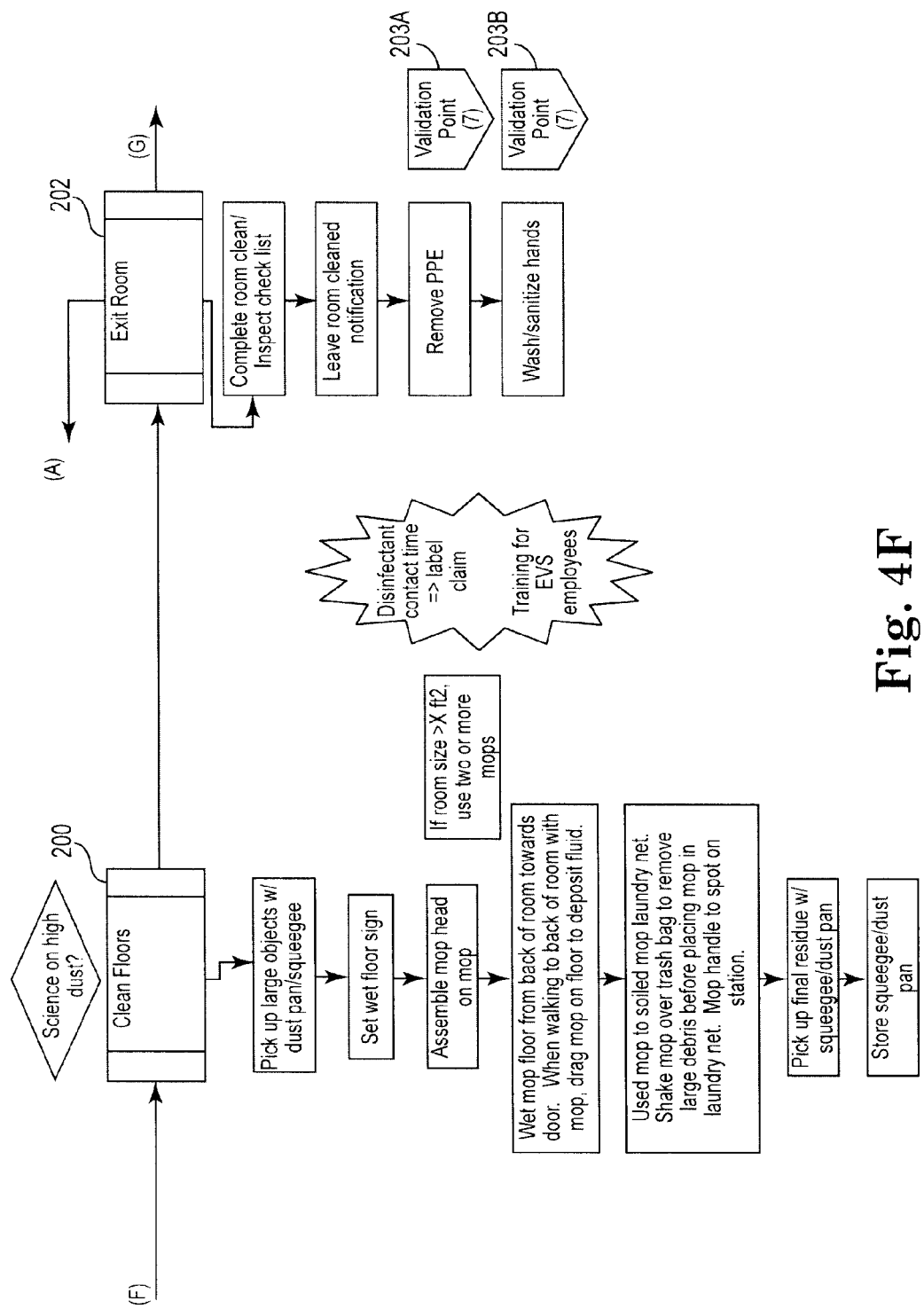

FIG. 4F shows an example of a "Clean Floors" main process step (200). This step may include several sub-steps, including picking up of large objects with a dust pan or squeegee, setting up a wet floor sign, assembling a mop head on a mop, specific procedures for mopping the floor, specific procedures for returning used mop to soiled laundry net and replacing mop handle on cleaning station, storing of the squeegee/dust pan, etc.

FIG. 4F also shows an example of an "Exit Room" main process step (202). This step may include the sub-steps of completing a room cleaning inspection checklist, leaving the room cleaned notification, removal of PPE, and post-room cleaning hand washing/sanitizing. Validation points (203A-203B) occur during the removal of PPE and hand washing steps, to ensure proper handling and/or disposal of the PPE and to confirm proper post-room cleaning hand washing takes place.

Figure 4G:
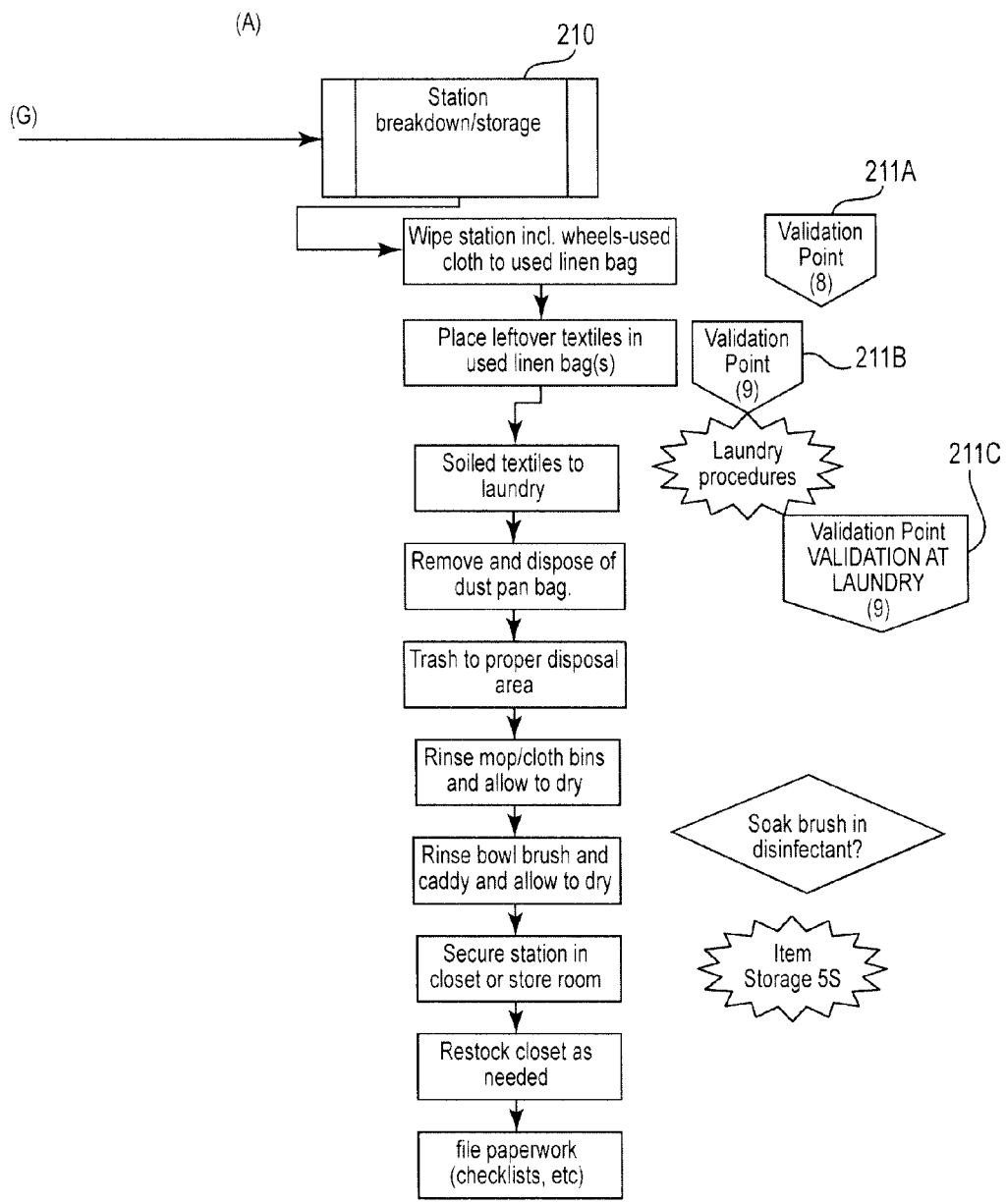

FIG. 4G shows an example of a "Station Breakdown/Storage" main process step (210). This step may include wiping of the cleaning station, placing of used cleaning cloths to the used linen bag, placing of leftover textiles (unused) in the used linen bag, sending of soiled textiles to the laundry, proper disposal of trash. This may also include rinsing of mop and cloth bins and allowing them to dry, rinsing of bowl brush and caddy and allowing them to dry. The station may be secured in a closet or store room. The closet may be restocked as needed. The process may also require cleaning personnel to file paperwork and/or checklists.

Validation point (211A) occurs when the cleaning station is wiped down with disinfectant. Here, validation of various cleaning procedures parameters to ensure that the patient room is properly cleaned and sanitized are monitored. For example, the validation point (211A) may require that all relevant surfaces of the cleaning station have been contacted with a disinfectant impregnated cloth and remain wet for at least 10 minutes (or other appropriate time corresponding with the disinfecting time of the product) with disinfectant. Monitoring may be accomplished via visual inspection of how long surfaces remain wet, photo- or chemiluminescent indicators, adenosine triphosphate (ATP), culture, etc., to ensure that proper cleaning/sanitizing procedures on the cleaning station were adequately performed.

Validation point(s) (211B-211C) occurs at the laundry site, where monitoring and validation of proper laundry procedures are performed to ensure proper handling/cleaning/disinfecting of laundry articles. Different laundry articles, such as cleaning cloths, bed linens, towels, gowns, etc., may have different laundry validation procedures.

FIG. 5 is a flow chart illustrating an example storage process map for the patient room module (220). The storage process map for each module includes proper storage/handling procedures for all of the products, tools and equipment used during the cleaning process map for that module. Thus, the storage process map for the patient room module may include storage/handling procedures for the patient room cleaning station and tools, any cleaners and/or disinfectants used during the patient room cleaning process, textiles needed during the room cleaning process, miscellaneous station supplies used during the room cleaning process, and mops or other cleaning equipment used during the room cleaning process. The storage process map may include storage conditions for each item, such as the storage location, conditions, temperature, maximum storage time, etc.

FIGS. 6A-6B are a chart listing example validation processes for the patient room module (230). The validation points in the left-most column correspond to the validation points shown in the flow charts of FIGS. 4A-4G. FIG. 6 shows, from left to right, identification of the validation point (corresponding to the like numbered validation point in FIGS. 4A-4G), identification of the process step at which the validation point occurs, description of the monitoring procedure, including what, how, frequency, and who will perform the monitoring procedure, and identification of possible corrective action should the validation indicate that the process parameters were not satisfied. Although the flow chart of FIG. 6 illustrates validation processes for these validation points, it shall be understood that other or different validation points and their associated processes may also be used for the patient room module, and that the invention is not limited to or by the examples given herein.

Figure 7:
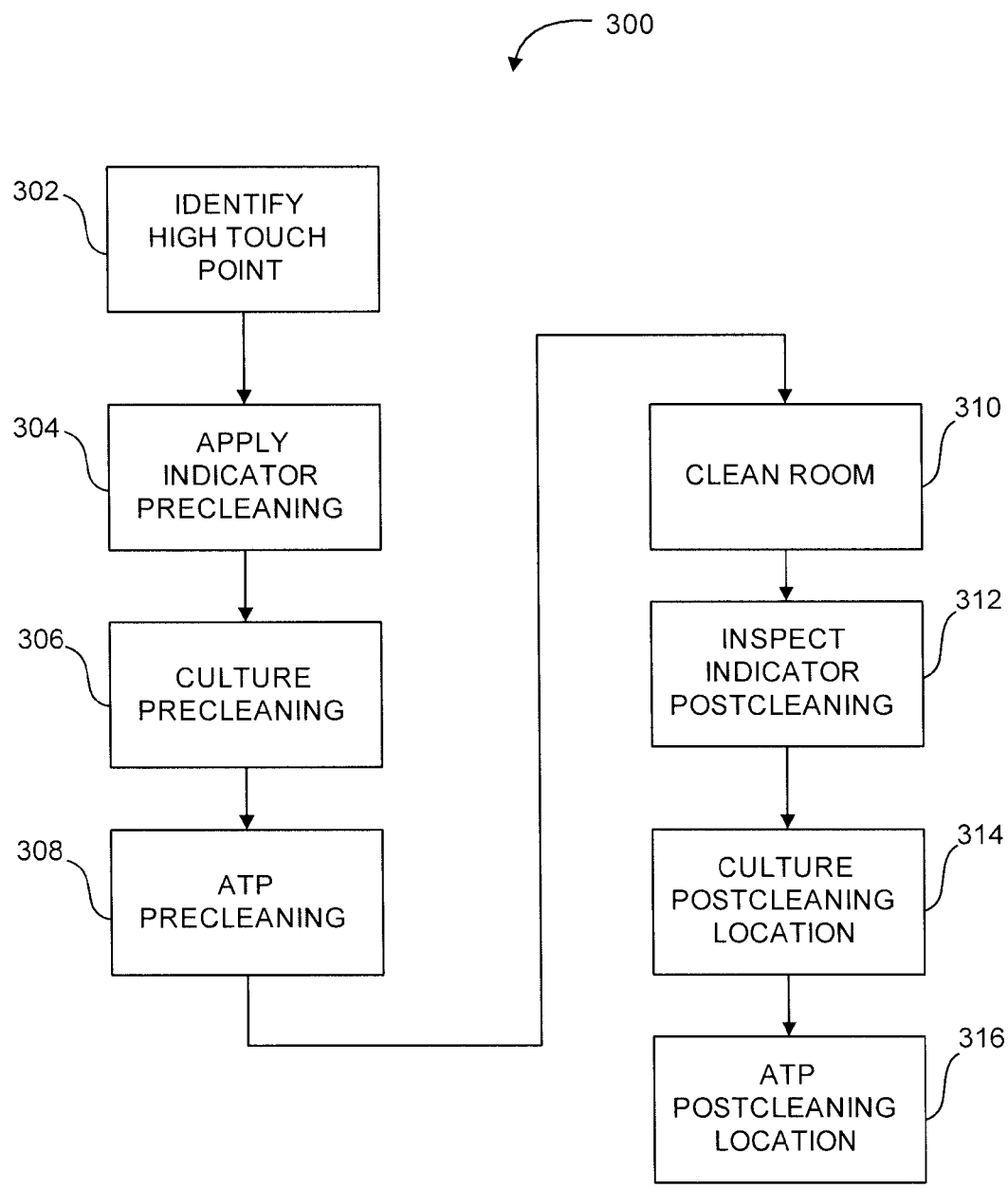
FIG. 7 is a flow chart illustrating an example high touch object cleaning validation process 300 for the patient room module.

FIG. 7 is a flow chart illustrating an example high touch object cleaning validation process 300 for the patient room module. It shall be understood that this process is one example that may be used with a particular high touch object, and that other high touch objects may have similar or different validation processes depending upon the particular requirements for each high touch object, and that the invention is not limited in this respect.

Process 300 includes various testing methods that may be used to evaluate the effectiveness of the room cleaning. The testing may be performed both before and after the patient's room has been cleaned. Process 300 begins with identification of the particular high touch object involved (302). For example, high touch objects for the patient room module may include the sink, the toilet handle, the toilet seat, the bed pan cleaner, the toilet hand hold/rail, the bathroom door handle, the bed rail, the call button, the tray table, the bedside table, the telephone, and the room door knob.

One such test may include application of an indicator, such as a photoluminescent or chemiluminescent indicator, which is applied to a defined location on the high touch point prior to cleaning (304). Inspection of the indicator post cleaning may be used to determine whether the high touch object has been cleaned. In the patient room module, for example, the indicator would be applied in a well-defined manner to each of the high touch objects that are defined for that module. After completion of the cleaning procedure (310), the surface may be inspected with a black light to determine if the indicator was disturbed by the cleaning process (312). Training would be provided to hospital personnel on what constitutes a "passing" or "failing" result. For example, passing results may include complete removal of the indicator or disturbance of a circular swirl pattern. Failing results may include an untouched indicator and/or no evidence of wiping.

Another test may include examination of culture counts as an indication of cleaning effectiveness. A surface sample of aerobic culture counts are collected at defined locations on the surface of the high touch object before (306) and after (314) completion of the cleaning process. Presence of aerobic bacteria may be used to quantify cleaning effectiveness. Threshold levels for "passing" or "failing" aerobic culture counts may be set, or the total aerobic culture count may be stored and reported.

Another test may include examination of adenosine triphosphate (ATP) levels as indication of cleaning effectiveness. Defined locations on the surface of the high touch object are swabbed before (308) and after (316) completion of the cleaning procedure (310). Presence of ATP correlates with presence of microorganisms, and thus may be used to quantify cleaning effectiveness. Threshold levels for "passing" or "failing" ATP levels may be set, or the total ATP level may be stored and reported.

Training/certification may be provided to the relevant personnel to help ensure that the methodologies of the validated hospital cleaning method are followed. Consistent application by trained personnel of the methodologies described herein helps to increase accuracy and reliability of the validated hospital cleaning methods. For example, detailed instructions concerning application of the indicator may include the delivery method with which the indicator is applied (gel pen, swab, etc.) and how the indicator should be applied (swirl pattern, dot, etc.) may be provided. Similarly, detailed instructions concerning collection of ATP or culture samples (size of swab or culture, etc.) may also be provided. Information regarding the specific location at which the indicator should be applied or from where the ATP or culture should be taken (faucet post vs. faucet handle; near end of faucet handle vs. far end of faucet handle; top or bottom of flange of toilet flush; back, left or right side of toilet seat; location on toilet hand rail, etc.) may also be provided.

The data collected from verification process 300, as well as from all of the other verification processes of the validated hospital cleaning method, may be input manually (such as for visual inspection of the indicator or ATP or culture counts) or automatically for those pieces of data obtained from automated equipment.

FIGS. 8A-8L show example reports that may be generated by reporting application 34 for the patient room module for a fictional healthcare facility, ABC Hospital. These reports may include, for example, detailed analysis and reporting on key metrics, including cleaning outcomes, behavioral observations, room cleaning efficiency, products/tools overview, dispenser analysis, staff knowledge, employee satisfaction, patient satisfaction, etc. The reports may benchmark current module practices across the entire database or across hospitals or other healthcare facilities. The reports may include trending of various key metrics over time, provide actionable improvement plans and assess current practices relative to best practices and process critical control points. It shall be understood that the reports shown in FIGS. 8A-8L are exemplary only, and that other reports may also be generated for the patient room module, and that other reports may also be generated for other modules, each including reports on data relevant to those modules, and the invention is not limited in this respect.

FIG. 8A, for example, illustrates an example summary report for the fictional healthcare facility. The summary report shows a table having rows for each of continuous improvement and education, operational processes, hygiene outcome efficiency, and satisfaction. The data for each of these rows is shown across columns for the facility wide baseline, the previous period, and the current period.

FIG. 8B, for example, illustrates an example report including data regarding hygiene outcomes for the marking solution, indicating the percent of time high touch objects were cleaned. In this particular example, the data is broken down in overall high touch point cleaning, patient room cleaning and bathroom cleaning, with columns for the facility wide baseline, the previous period and the current period. Also shown are data for the most cleaned high touch point, the most frequently missed high touch point and the percentage of time all high touch points are cleaned.

FIG. 8C, for example, illustrates an example report including detailed analysis of the percent of time high touch objects were cleaned. This table gives data for each individual high touch point for the facility wide baseline, the previous period and the current period.

Figure 8D:
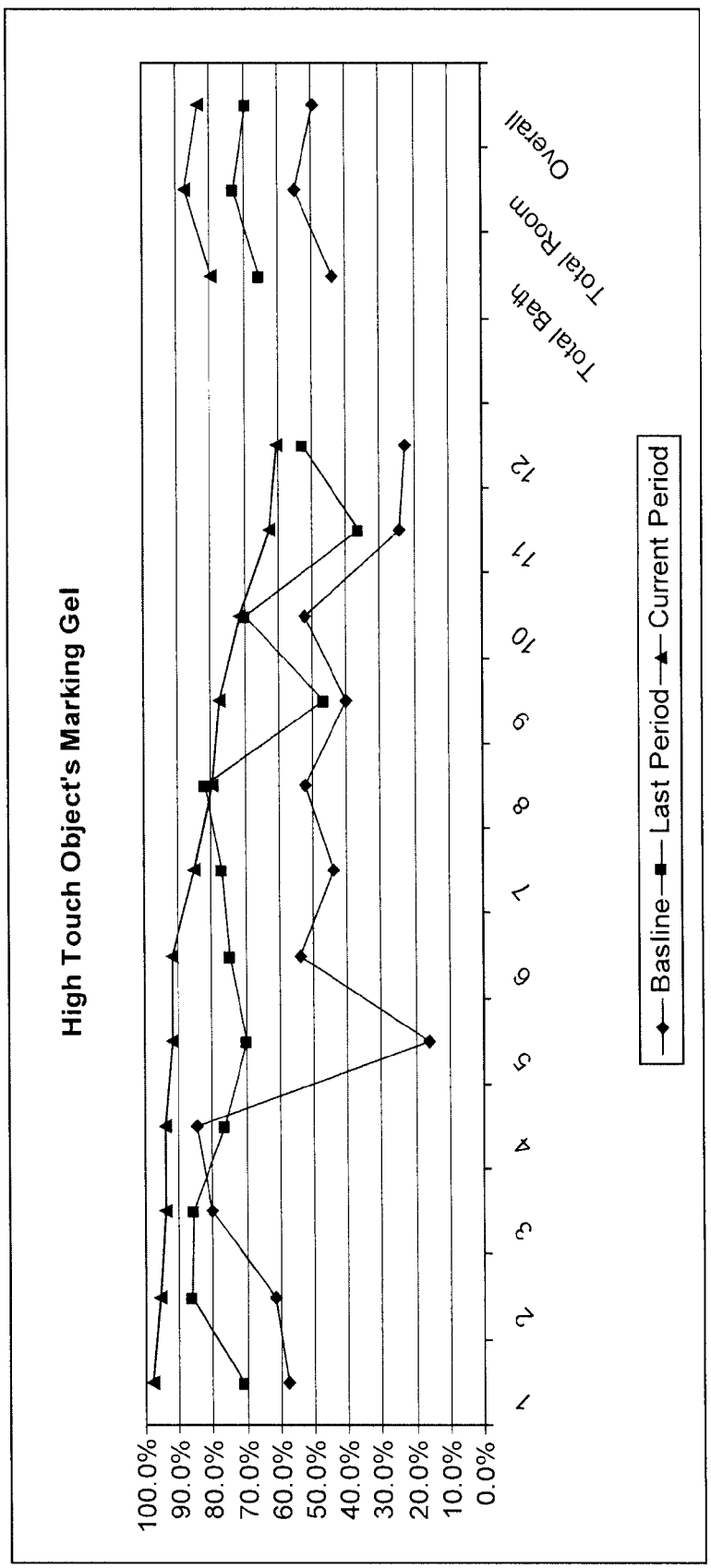

FIG. 8D, for example, illustrates an example report that shows the detailed analysis of the percent of time high touch objects were cleaned for each individual high touch object in graphical form.

FIG. 8E, for example, illustrates an example report including data regarding hygiene outcomes for culturing of high touch points. The table shows percent occurrences where the post-cleaning reading was lower than the pre-cleaning reading. The report also shows which high touch point had the lowest average culture count and which had the high average culture count.

FIG. 8F, for example, illustrates an example report showing, in tabular form, analysis of the percent occurrences where the where the post-cleaning reading was lower than the pre-cleaning reading for each individual high touch point. This example report includes the data in graphical and tabular form.

Figure 8G:
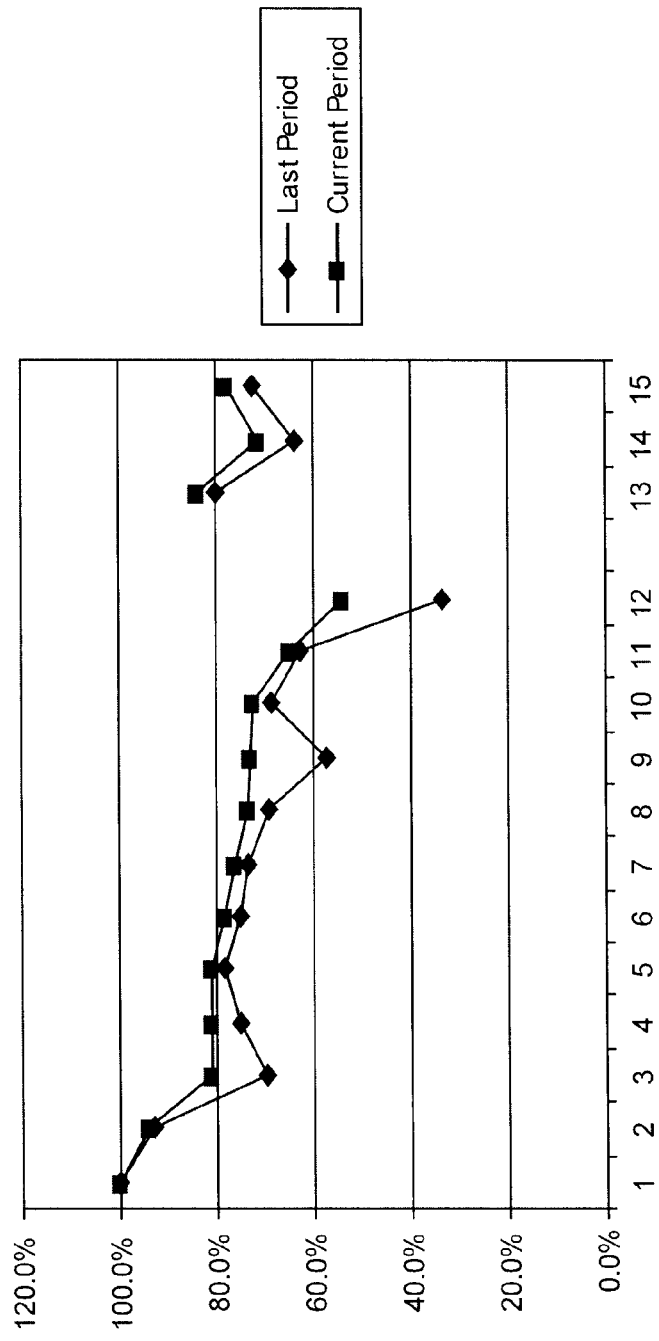

FIG. 8G, for example, illustrates an example report showing, in graphical form, analysis of the percent occurrences where the post-cleaning reading was lower than the pre-cleaning reading for each individual high touch point.

Figure 8H:
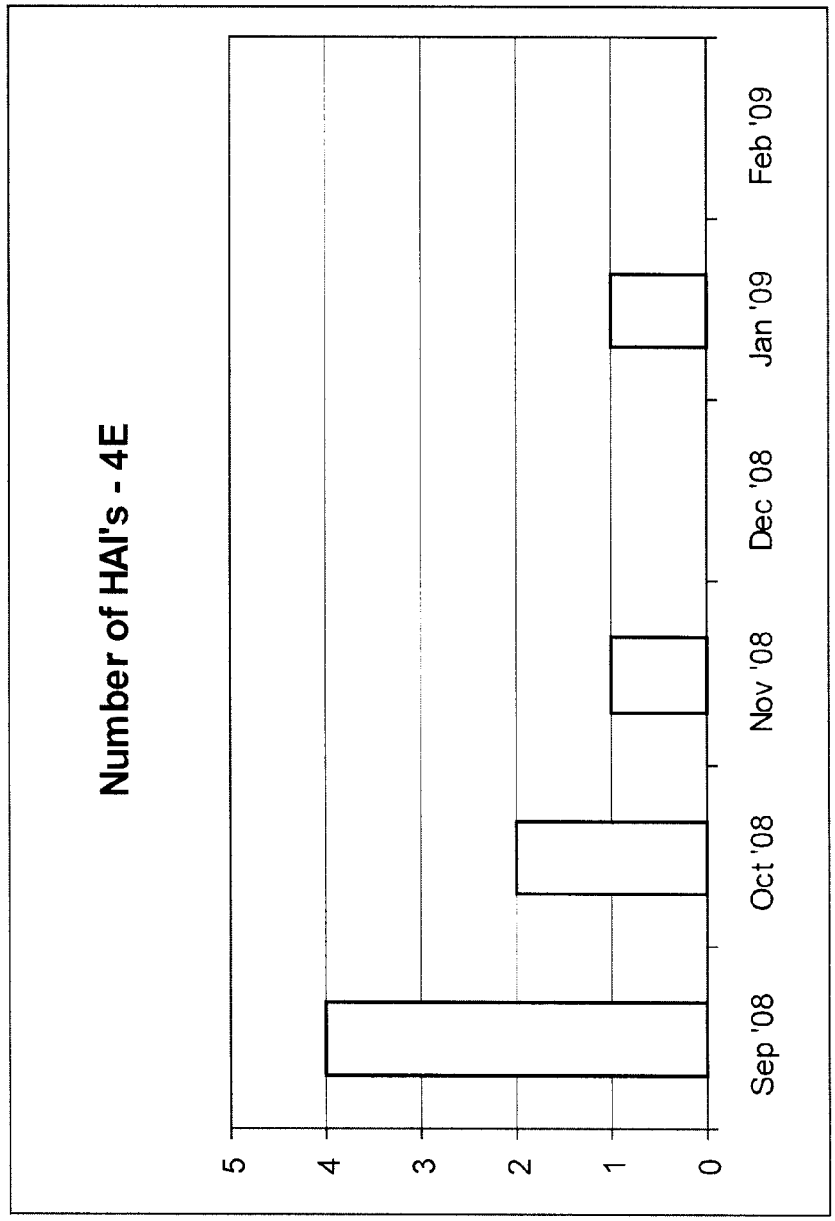

FIG. 8H, for example, illustrates an example report detailing the number of hospital acquired infections by month over a period of time. In this example, the period September '08 may be the baseline (i.e., data taken before the validated hospital cleaning method was in place to establish a basis for comparison), whereas the period January '08 is the current period.

Figure 8I:
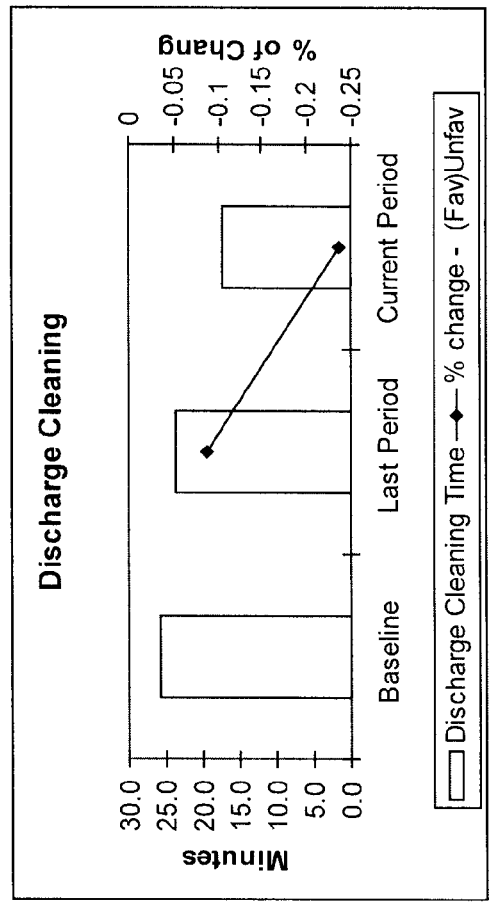

FIG. 8I, for example, illustrates an example report detailing operational efficiency for cleaning upon discharge. This table allows users to compare current operational efficiency with baseline operational efficiency to determine whether the operational efficiency associated with the validated hospital cleaning method is within acceptable limits or whether it favorably compares to the baseline operational efficiency.

Figure 8J:
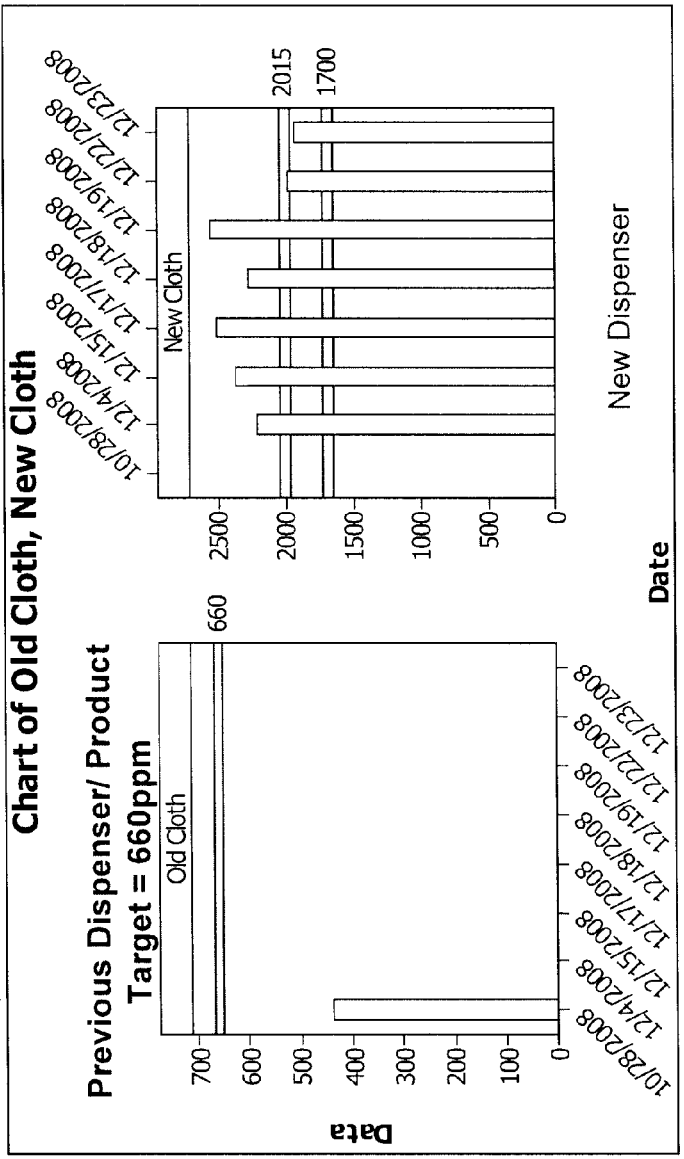

FIG. 8J, for example, illustrates an example report detailing operational efficiency for disinfectant concentration as applied to surfaces for a previous cleaning cloth and dispenser and the current cleaning cloth and dispenser.

FIG. 8K, for example, illustrates an example report detailing operational efficiency for disinfectant concentration as dispensed by the current dispenser. The report indicates whether the disinfectant concentration is within acceptable limits and whether it met the target concentration.

FIG. 8L, for example, illustrates an example report detailing operational efficiency with respect to behavior observations of cleaning personnel. This information can help to identify where additional training may be necessary if identified behaviors are not conforming to the methodologies of the validated hospital cleaning method.

FIG. 8M, for example, illustrates an example report providing a summary of recommended next steps that the hospital may take to improve their results in the future. Suggested next steps are given for each of continuous improvement and education, operational processes, hygiene outcome efficiency, and satisfaction.

Various modules and validation processes of the validated hospital cleaning system/method described herein may include infection prevention solutions including chemistries, equipment, dispensing, packaging, effective utilization processes, validation and auditing methods and ease-of-use automation technologies. These may include, for example, high level disinfectants, patient bathing/wipe/wash, equipment draping, site prep, wound cleaning, cart washing, floor tacky mats, patient screening/ID, patient pre-admission kits, room decontaminants, long life hard surface disinfectant, soft surface mist/vapor cleaning, ice machine conditioning, air filtration, visitor barriers/screens/kits, operating room cleaning solution, patient room cleaning solution, general instrument clean/sanitize, GI device clean/disinfect, fluid management/disposal, systems for cleaning/sanitizing, sensors/monitors/tracking devices, etc.

The validated hospital cleaning system/method may incorporate tools for data utilization and process improvements such as data collection, analysis, utilization and interpretation to achieve process improvements, behavioral changes and outcome measures. For example, the validated hospital cleaning method may include tools and technology to gather/manage information, outcome data collection, data analysis and utilization, peer hospital comparisons, industry metrics/standards.

The validated hospital cleaning system/method may also include quality assurance, such as oversight and monitoring of labor providers to assure cleaning and disinfection quality across the hospital to reduce the spread of HAIs (hospital staff, outside provider employees, contractors, etc.). Quality control may also receive input from various automated machines, such as chemical dispensers that dispense various cleaning solutions, to ensure that the concentration of active ingredient in a disinfectant or other chemical is within certain limits, that the appropriate amounts are being dispensed, etc.

The validated hospital cleaning process may capture many demographics as well as measure the effectiveness of following of the validated cleaning process. The data may include, for example, information related to room cleanliness, patient satisfaction scores, HAI infection risks and others. The data may be used as a feed back loop to assure the system has been followed as prescribed in the validated process which has been shown to yield improved results in these three areas. The validated hospital cleaning system/process may include capturing a baseline status of the cleanliness of the room or the cleanliness of each module within a hospital or other healthcare facility.

As described herein, some parts of the validated hospital cleaning process may be computer implemented, and as such may be incorporated into computer software or hardware. For example, a computer system may collect and analyze data generated during implementation of the validation processes. A computer implemented system may analyze data to determine whether a particular validation point has been satisfied, and may perform statistical analysis on a process, module or hospital-wide basis. This information may be stored and analyzed and reports generated to provide feedback to a facility manager or corporation. Furthermore, the analysis may be performed across multiple accounts, such as multiple accounts within a single corporation or organizational region, to compare, for example, one hospital in a corporation with other hospitals within the same corporation or to compare like modules of multiple hospitals.

The techniques described herein may be implemented in hardware, software, firmware or any combination thereof. If implemented in software, the techniques may be realized at least in part by a computer-readable medium comprising instructions that, when executed by computer of a validated healthcare processing system cause the computer to perform one or more of the techniques of this disclosure. The computer-readable data storage medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, a magnetic disk or a magnetic tape, a optical disk or magneto-optic disk, CD, CD-ROM, DVD, a holographic medium, or the like. The instructions may be implemented as one or more software modules, which may be executed by themselves or in combination with other software.

The computer-readable instructions may be executed in the computer of the system by one or more processors, general purpose microprocessors, ASICs, FPGAs or other equivalent integrated or discrete logic circuitry.

The instructions and the media are not necessarily associated with any particular computer or other apparatus, but may be carried out by various general-purpose or specialized machines. The instructions may be distributed among two or more media and may be executed by two or more machines. The machines may be coupled to one another directly, or may be coupled through a network, such as a local access network (LAN), or a global network such as the Internet. Accordingly, the term "processor," as used herein may refer to any structure suitable for implementation of the techniques described herein.

The invention may also be embodied as one or more devices that include logic circuitry to carry out the functions or methods as described herein. The logic circuitry may include a processor that may be programmable for a general purpose or may be dedicated, such as microcontroller, a microprocessor, a Digital Signal Processor (DSP), an Application Specific Integrated Circuit (ASIC), a field programmable gate array (FPGA), and the like.

One or more of the techniques described herein may be partially or wholly executed in software. For example, a computer-readable medium may store or otherwise comprise computer-readable instructions, i.e., program code that can be executed by a processor to carry out one of more of the techniques described above.

The validated hospital cleaning method may also incorporate healthcare worker training and continuing education, such as teaching new or ongoing skills and changing paradigms and behaviors within hospitals. These may include, for example, central sterile on-site process training/validation/usage, compliance/ procedural training, training oversight/monitoring/interventions, comprehensive training to impact outcomes, medical school and association curriculum, certification training, etc. This may include both upfront and periodic refresher training, training materials and a training process created for each module to assure the housekeepers are following the best practice process and using the proper tools and products to assure the use of the validated process will yield the outcome of a clean room or module, and possibly a reduced HAI risk.

The validated hospital cleaning system and method thus provides a comprehensive, hospital-wide cleaning and sanitization practice that addresses cleaning, disinfection sterilization and clinical solutions that may increase hospital cleanliness and may reduce the spread of HAIs. Advantages of the validated hospital cleaning system and method may be documented improvements in environmental sanitation, perceptible room cleanliness, patient satisfaction scores, and HAI risk reduction and associated cost savings. Advantages may also include fewer patient deaths and patient complications due to HAIs. The validated hospital cleaning system and method may also provide cost reductions through improved operational efficiencies and a reduction in health care worker errors and inconsistencies.

Although the validated hospital cleaning system and method has been described with respect to hospitals or other healthcare facilities, it shall be understood that this concept may also be applied to the cleaning and sanitation best practice in many different enterprises in which an integrated approach to cleaning and/or sanitizing a portion of a facility or an entire facility is desired. For example, the modular validated hospital cleaning system and method may be adapted for use in applications such as hotel room cleaning, education facilities, long term care, restaurants, food service, food and beverage facilities, eating areas, rest rooms, food preparation areas, cooking areas, etc.

Various embodiments of the invention have been described. These and other embodiments are within the scope of the following claims.

The invention claimed is:

1. A system comprising:
   a server computer that receives collected data from a healthcare facility, the collected data based on monitored validation points within a plurality of cleaning process maps for the healthcare facility, each of the cleaning process maps corresponding to a different one of a plurality of modules within the healthcare facility and defining housekeeping procedures associated with the corresponding module;
   a database coupled to the server computer that stores the collected data from the healthcare facility in association with hospital data that uniquely identifies the healthcare facility, that stores module data that defines each of the plurality of modules within the healthcare facility, and that stores the plurality of cleaning process maps in association with the corresponding module data;
   an analysis application resident on the server computer that analyzes the collected data and generates therefrom validation data indicative of adherence to the housekeeping procedures within the healthcare facility; and a reporting application resident on the server computer that generates reports that characterize the cleanliness of the healthcare facility based on the collected data, the validation data, the hospital data and the module data;

each cleaning process map further including a storage process and a validation process, the storage process defining storage conditions for cleaning products, tools, and textiles, the validation process defining one or more of the validation points indicative of cleanliness of the associated module within the healthcare facility, the validation process further defining a monitoring procedure for each of the one more validation points and identifying corrective action in the event that one or more of the validation points are not satisfied.

2. The system of claim 1, wherein the server computer is located remotely from the healthcare facility.

3. The system of claim 1, wherein the server computer is local to the healthcare facility.

4. The system of claim 1, wherein at least one of the validation points comprises a target parameter specifying a desired characteristic for a component of one of the validation processes.

5. The system of claim 1, wherein at least one of the validation points comprises a target parameter specifying a minimum disinfectant concentration.

6. The system of claim 5, wherein the analysis application determines whether a dispensed disinfectant meets the target parameter for the minimum disinfectant concentration.

7. The system of claim 1, wherein the analysis application analyzes collected data from a first time period to generate first validation data and collected data from a second time period to generate second validation data.

8. The system of claim 1, wherein the reporting application generates a report that compares the first validation data with the second validation data.

9. The system of claim 1, wherein the database stores baseline data corresponding to status of the monitored validation points before implementation of the validation processes.

10. The system of claim 9, wherein the reporting application generates reports comparing collected data from a current time period with the baseline data.

11. The system of claim 1, wherein the reporting application generates reports identifying whether the validation points for each module were satisfied.

12. The system of claim 1, wherein the reporting application generates reports identifying which validation points in a module were satisfied.

13. The system of claim 1 further including at least one input device into which the collected data is entered.

14. The system of claim 13 wherein the at least one input device includes one or more of a laptop computer, a personal digital assistant, or a cell phone.

15. The system of claim 13 wherein the at least one input device comprises an electronic device into which the collected data is entered.

16. A method comprising:

storing, in a database, a plurality of modules within the healthcare facility, each module associated with a physical area within the healthcare facility or with a function performed within the healthcare facility;

associating each of the plurality of modules with a different one of a plurality of cleaning process maps;

storing, in the database, the plurality of cleaning process maps, each of the cleaning process maps defining housekeeping procedures for the associated module, each cleaning process map further including a storage process and a validation process, the storage process defining storage conditions for cleaning products, tools, and textiles, the validation process defining one or more of the validation points indicative of cleanliness of the associated module within the healthcare facility, the validation process further defining a monitoring procedure for each of the one more validation points and identifying corrective action in the event that one or more of the validation points are not satisfied;

receiving, at a processor, collected data associated with monitored validation points specified in one or more of the cleaning process maps; and analyzing the collected data, using the processor, to generate validation data indicative of adherence to the housekeeping procedures within the healthcare facility.

17. The method of claim 16, wherein defining modules within the healthcare facility comprises defining at least one of a patient room module, a critical care module, a central sterile processing module, an operating room module, a food service module, a bathroom module, or a laundry room module.

18. The method of claim 16, wherein defining modules comprises defining at least one of a patient skincare module, a wound cleansing module, or a hand hygiene module.

19. The method of claim 16, further including correlating each of the plurality of modules with one or more contamination vectors.

20. The method of claim 19, further including generating one of the plurality of cleaning process maps based on the associated module and the contamination vectors correlated with the associated module.

21. The method of claim 16, further including training staff of the healthcare facility regarding the cleaning process maps.

22. The method of claim 16, further including re-training staff of the healthcare facility when the process parameters associated with certain of the monitored validation point are not satisfied.

23. The method of claim 16, further including generating validation data, using the processor, based on whether the process parameters associated with each monitored validation point are satisfied.

24. The method of claim 23, further including generating reports, using the processor, based on the validation data.

25. The method of claim 16 further comprising entering the collected data into an input device.

26. The method of claim 16 further comprising entering the collected data into at least one of a laptop computer, a personal digital assistant, or a cell phone.

27. The method of claim 16 further comprising entering the collected data into an electronic device.

28. A non-transitory computer-readable medium comprising instructions that upon execution in a computer of a validated hospital cleaning processing system cause the computer to:

receive collected data from a healthcare facility, the collected data based on monitored validation points within a plurality of validation processes for the healthcare facility;

store the collected data from the healthcare facility in association with hospital data that uniquely identifies the healthcare facility;

store module data that defines modules within the healthcare facility;

store process map data that defines at least one cleaning process map for each module within the healthcare facility, each of the cleaning process maps defining housekeeping procedures for the associated module, each cleaning process map further including a storage process and a validation process, the storage process defining storage conditions for cleaning products, tools, and textiles, the validation process defining one or more of the validation points indicative of cleanliness of the associated module within the healthcare facility, the validation process further defining a monitoring procedure for each of the one more validation points and identifying corrective action in the event that one or more of the validation points are not satisfied;

analyze the collected data with respect to the process map data and generate therefrom validation data indicative of adherence to the housekeeping procedures within the healthcare facility; and generate at least one report that characterizes adherence to the housekeeping procedures within the healthcare facility based on the collected data, the validation data, the hospital data and the module data.

* * * * *